US010977702B2

(12) United States Patent
Patel et al.

(10) Patent No.: US 10,977,702 B2
(45) Date of Patent: Apr. 13, 2021

(54) PROSPECTIVE MANAGEMENT SYSTEM FOR MEDICAL BENEFIT PRESCRIPTIONS

(75) Inventors: Minalkumar Patel, Weehawken, NJ (US); Mohan P. Charles, St. Louis, MO (US); Melissa Sampson, N. Richland Hills, TX (US); Michael Escuder, Flushing, NY (US)

(73) Assignee: AXON HEALTHCARE SERVICES, INC., Southlake, TX (US)

( * ) Notice: Subject to any disclaimer, the term of this patent is extended or adjusted under 35 U.S.C. 154(b) by 723 days.

(21) Appl. No.: 13/107,322

(22) Filed: May 13, 2011

(65) Prior Publication Data

US 2011/0282689 A1    Nov. 17, 2011

Related U.S. Application Data

(60) Provisional application No. 61/334,242, filed on May 13, 2010.

(51) Int. Cl.
*G06Q 30/06* (2012.01)
*G16H 15/00* (2018.01)
(Continued)

(52) U.S. Cl.
CPC ......... *G06Q 30/0603* (2013.01); *G06Q 40/08* (2013.01); *G16H 10/60* (2018.01); *G16H 15/00* (2018.01); *G16H 20/13* (2018.01)

(58) Field of Classification Search
CPC .... G06Q 30/0603; G06Q 40/08; G16H 15/00; G16H 20/13; G16H 10/60
See application file for complete search history.

(56) References Cited

U.S. PATENT DOCUMENTS 6,088,677 A    7/2000  Spurgeon
6,317,719 B1   11/2001  Schrier
(Continued)

OTHER PUBLICATIONS

Stern, Debbie, Reissman, Debi; Specialty Pharmacy Cost Management Strategies of Private Health Care Payers; Journal of Managed Care Pharmacy—JMCP; Nov./Dec. 2006, vol. 12, No. 9, pp. 736-744.
(Continued)

*Primary Examiner* — Eliza A Lam
(74) *Attorney, Agent, or Firm* — Amster, Rothstein & Ebenstein LLP

(57) ABSTRACT

The present invention provides an interactive, electronic, knowledge-based ordering process for specialty/biotech pharmaceuticals (medically coded drugs) which results in less waste, improved procedural efficiencies, and greater cost savings than the current ordering systems. The knowledge-base of the system is based on the health plan's clinical policies as well as the status of the patient and their entitled benefits with the health plan, and it is applied in an interactive manner through a web-enabled system which provides a real-time, prospective examination and control over requests for authorization to dispense the medically coded drugs. The system also includes a feedback loop from the specialty pharmacies to provide information on the medicines that have actually been dispensed. The system also provides to the patient, educational material and adherence reminders to affect therapeutic outcomes.

18 Claims, 24 Drawing Sheets

(51) Int. Cl.
*G16H 20/13* (2018.01)
*G06Q 40/08* (2012.01)
*G16H 10/60* (2018.01)

(56) References Cited

U.S. PATENT DOCUMENTS

| | | | |
|---|---|---|---|
| 6,519,569 B1* | 2/2003 | White | A61M 5/142 604/151 |
| 7,493,264 B1 | 2/2009 | Kelly | |
| 7,617,116 B2 | 11/2009 | Amar | |
| 8,265,959 B2* | 9/2012 | McKenzie | G06Q 10/087 705/2 |
| 2002/0077857 A1* | 6/2002 | Seelinger | 705/2 |
| 2003/0078813 A1 | 4/2003 | Haskell et al. | |
| 2003/0135397 A1* | 7/2003 | Halow et al. | 705/4 |
| 2004/0073456 A1 | 4/2004 | Gottlieb | |
| 2004/0129716 A1* | 7/2004 | Naufel | G07F 17/0092 221/9 |
| 2005/0251416 A1 | 11/2005 | Greene | |
| 2006/0095298 A1 | 5/2006 | Bina | |
| 2008/0033751 A1* | 2/2008 | Greene | 705/2 |
| 2008/0275733 A1* | 11/2008 | Schmidt et al. | 705/3 |
| 2008/0288286 A1 | 11/2008 | Noreen | |
| 2009/0043608 A1* | 2/2009 | Nadas et al. | 705/3 |
| 2009/0198518 A1 | 8/2009 | McKenzie | |
| 2011/0282690 A1 | 11/2011 | Patel et al. | |

OTHER PUBLICATIONS

Health Information Designs; RxPert® Automated Prior Authorization System; Health Information Designs; www.hidinc.com/assets/files/RxPert_Medicaid_20090817.pdf; Inc.; circa 2009.

* cited by examiner

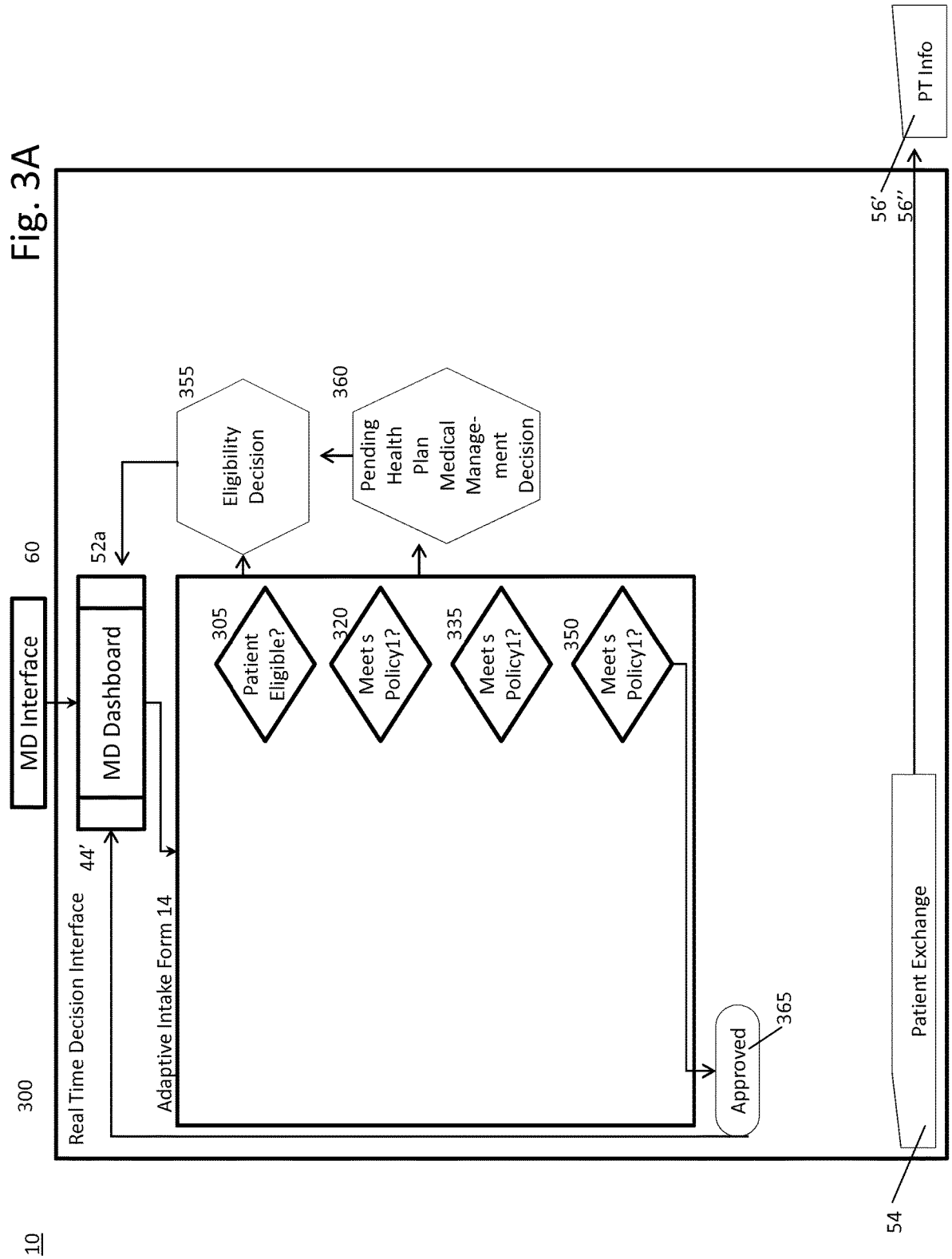

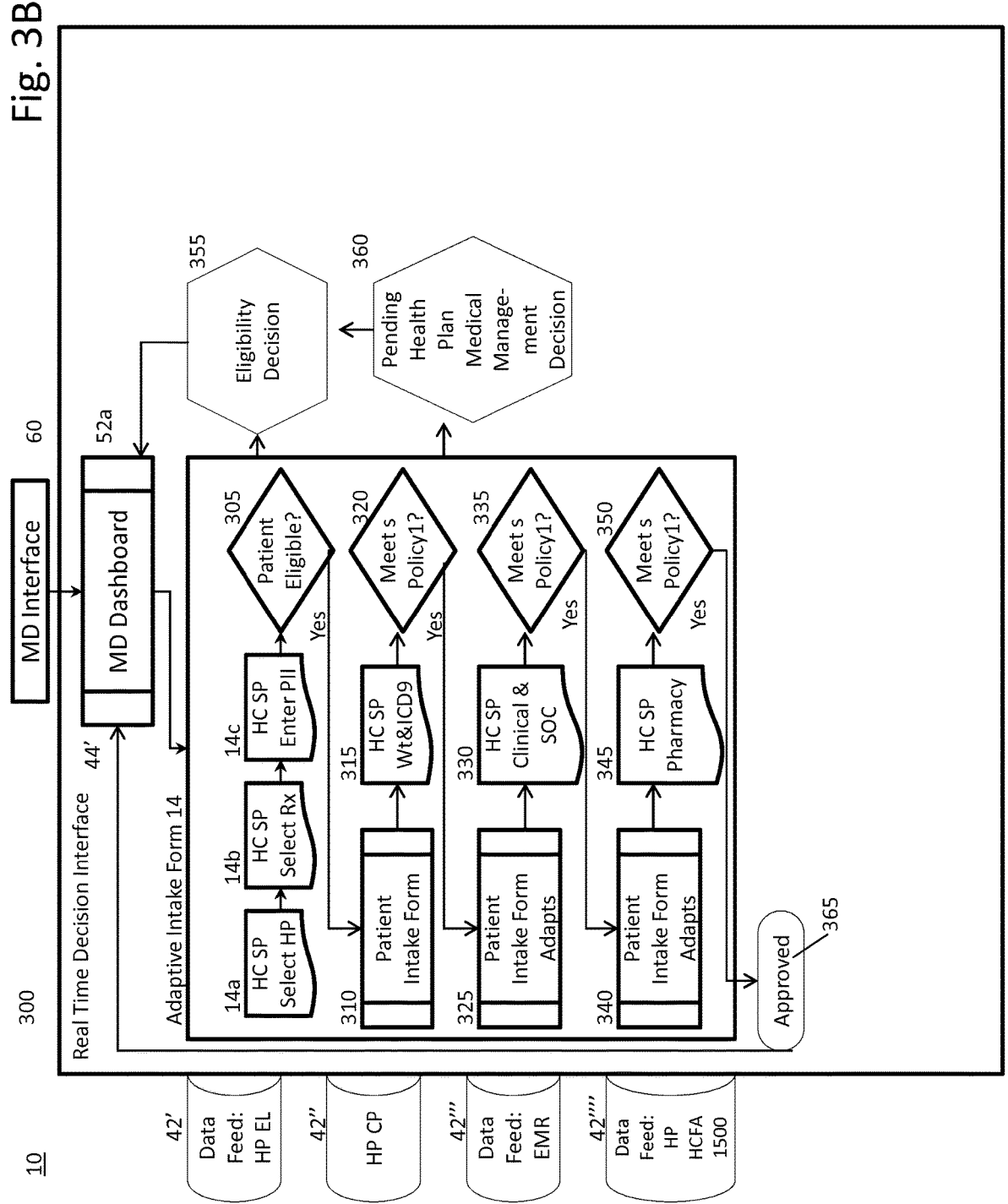

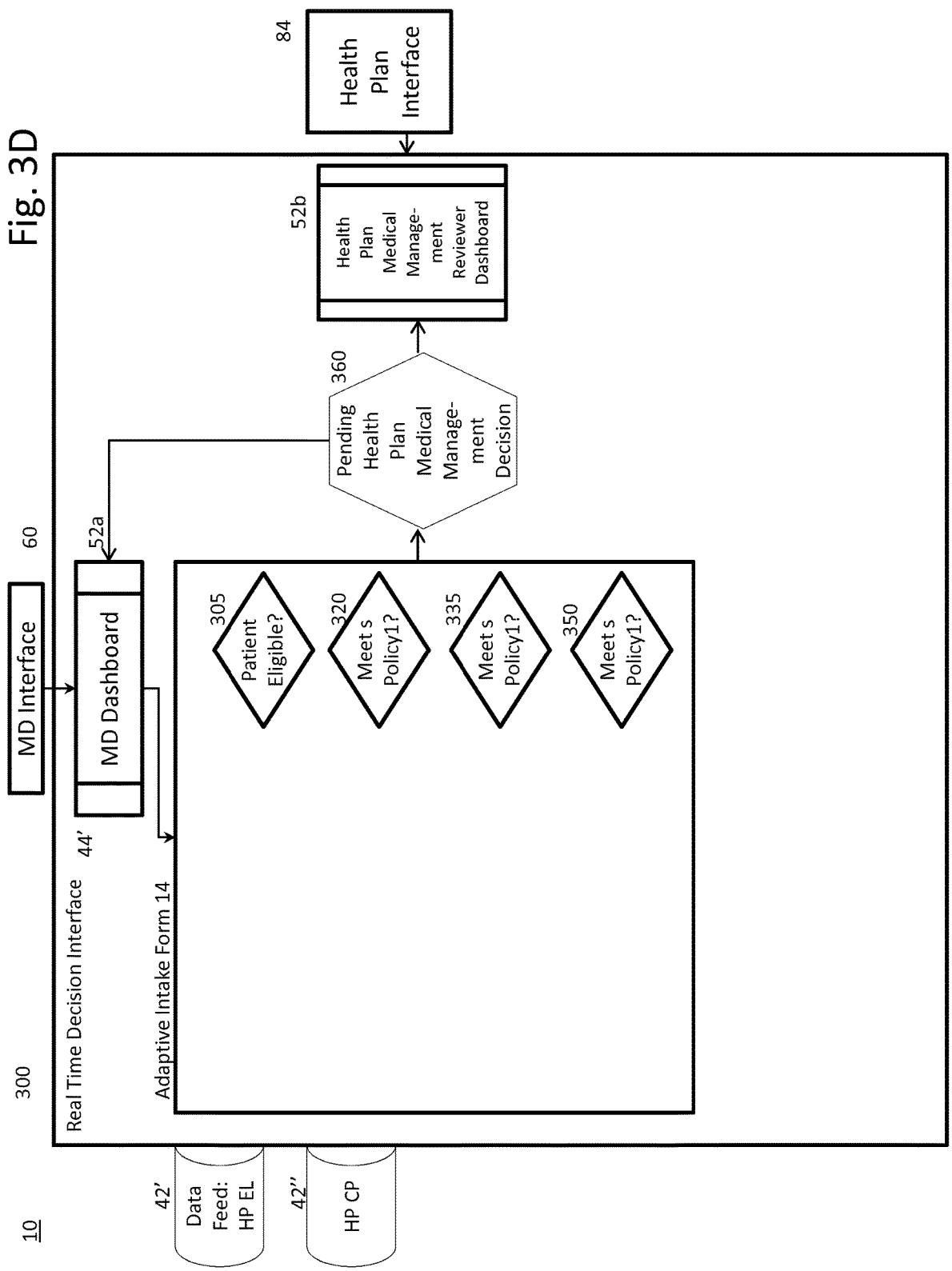

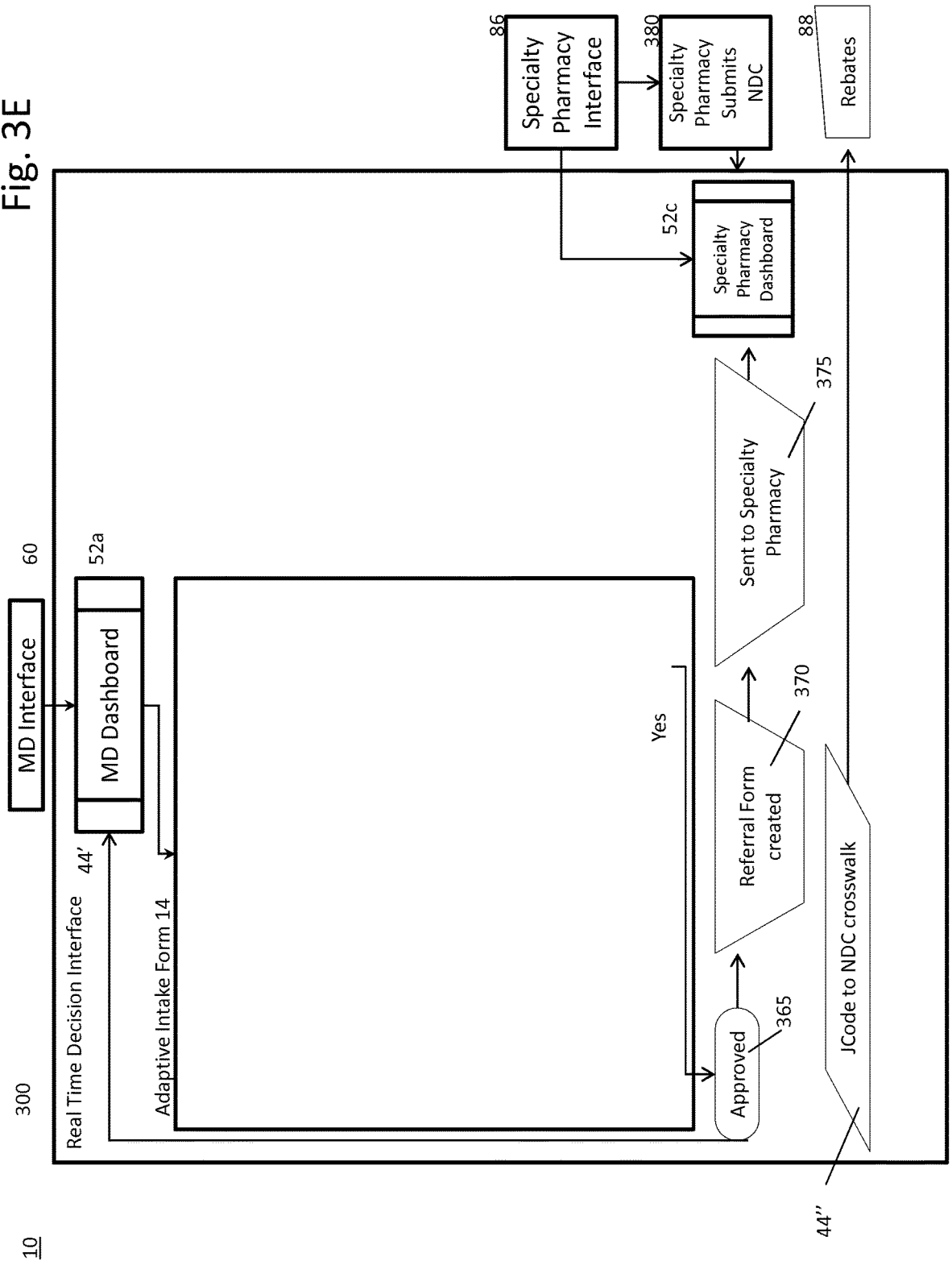

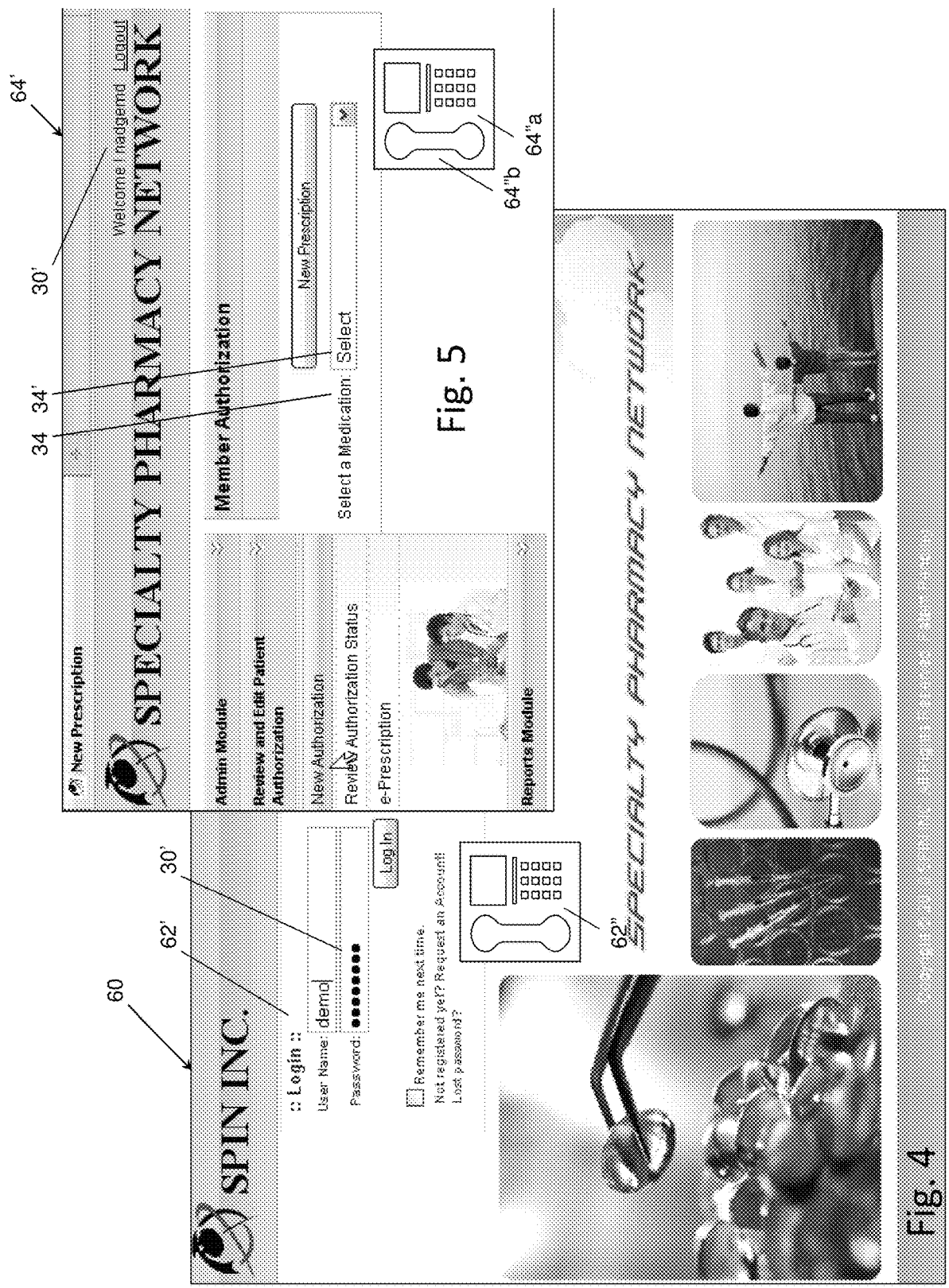

Drug Information

- Therapy: ● Initiation ○ Continuation
- Patient Weight In: 222 LBS OR
- Converted Value: ___ KG
- Drug Name: [Humira]
- Diagnosis Code: 555.0 - 555.9: Crohn's disease
- Drug Dose (MG/KG): 1 MG
- Therapy Duration: 4 Weeks
- CHF OR Immunosuppression: ● Yes ○ No

Pharmacy Information

- Pharmacy Network: Spin Pharmacy Network
- Need By Date: 04/29/2010 MM/DD/YY
- Validate the Prescription: [Validate Prescription]

Fig. 7B

Prescriber Information | Member Information | Drug Information | Member Details Summary

Drug Information

- Patient Weight In: 150 LBS OR
- Converted Value: ___ KG
- Therapy: ● Initiation ○ Continuation
- Drug Name: [_____]
- Diagnosis Code: 713.99 - 714.2, 714.4, 714.9: Rheumatoid Arthritis
- Drug Dose (MG/KG): [_____]
- Will patient be using Methotrexate concurrently? ● Yes ○ No
- Does patient have moderate to severely active Rheumatoid Arthritis? ● Yes ○ No
- Duration of Therapy (Weeks): 6 Weeks
- Dosage Calculation: [_____]
- Frequency of Administration: Select

BCBS Louisiana
Remicade® Pharmacy Order

Provided to NuFactor Pharmacy
41093 County Center Drive
Temecula, CA 92591
977-432-6258

40

| Patient Information: | | | |
|---|---|---|---|
| Patient Name: Remi Jones | Date Of Birth: 01/01/1940 | Physician Information: | |
| | | Physician Name: Melissa Sampson | |
| Insurance ID: 1234567890 | Policy Number: P29111955 | DEA#: 345-567 | NPI#: 111222333 |
| Group Number: ABC111111118 | Phone Number: 201-555-1212 | Office Phone: 201-555-1212 | email: mmd@care-int.com |
| Street Address: 555 Main Street 2A | State, Zip: Anytown, NJ 07030 | Street Address: 50 Harrison ST | State, Zip: Hoboken, NJ 54321 |
| Allergies: None | Patient Weight: 54 KG | Ship Medication To: Physician Office | |
| Prescription Information: | | | |
| Remicade® (Infliximab) 100 mg in 250ml vial | | Diagnosis Code: 713.00 Rheumatoid Arthritis | |
| Dose: 5 MG/KG | Frequency of Administration: Q8 Weeks | Duration of Therapy: 48 Weeks | Used with Methotrexate? YES |
| Number of Vials: 3 Vials; Administr | Need By Date: 3/21/2011 | Authorization#: 1234567987 | |
| Pharmacist must call Physician to obtain a Verbal Prescription | | | |
| BCBS LA Medical Management: 888-111-1234 | | | |

| Field | Value |
|---|---|
| Converted Value: | 60 KG |
| Drug Name: | REMICADE |
| Therapy: | ○ Initiation ● Continuation |
| Diagnosis Code: | 713.00 - 714.2, 714.4 - 714.9 Rheumatoid Arthritis |
| Drug Dose (MG/KG): | 12 MG |
| | / PENDING MEDICAL MGMT REVIEW |
| Will patient be using Methotrexate concurrently? | ○ Yes ● No |
| | / PENDING MEDICAL MGMT REVIEW |
| Does patient have moderate to severely active Rheumatoid Arthritis? | ○ Yes ● No |
| | / PENDING MEDICAL MGMT REVIEW |
| Duration of Therapy(Weeks): | 24 Weeks |
| Dosage Calculation: | 7 Vials |
| Frequency of Administration: | Q6 WEEKS |
| | / PENDING MEDICAL MGMT REVIEW |
| Does Patient Have a Negative TB Test: | ○ Yes ● No |
| | / PENDING MEDICAL MGMT REVIEW |
| CHF OR Immunosuppression: | ● Yes ○ No |

Warning : PRODUCT LABELING STATES PATIENTS TREATED WITH REMICADE ARE AT INCREASED RISK FOR INFECTIONS; PRODUCT LABELING STATES TO USE IN CAUTION IN PATIENTS WITH HEART FAILURE.

Fig. 9E

Dashboard

Drug Name: [All] [Show]   Filter records: [All]

| Auth ID# | Patient Name | Prescriber Name | Prescriber Phone Number | Drug | Diagnosis Code | Pharmacy | Date of Service | Need By Date | Status |
|---|---|---|---|---|---|---|---|---|---|
| 1234568094 | Remi jones | MELISSA MD | 201-111-1234 | REMICADE | 555.0 - 555.9: Crohn's disease | NuFACTOR Specialty Pharmacy | 10/01/2010 | 10/01/2010 | PENDING |
| 1234567895 | remi jones | MELISSA MD | 201-111-1234 | PEGASYS | 070.44 -- Chronic hepatitis C with hepatic coma | NuFACTOR Specialty Pharmacy | 10/01/2010 | 10/01/2010 | APPROVED |
| 1234567894 | remi jones | MELISSA MD | 201-111-1234 | PEGASYS | 070.44 -- Chronic hepatitis C with hepatic coma | NuFACTOR Specialty Pharmacy | 10/01/2010 | 10/01/2010 | APPROVED |
| 1234568093 | remi jones | MELISSA MD | 201-111-1234 | REMICADE | 713.00 - 714.2, 714.4 - 714.9 Rheumatoid Arthritis | NuFACTOR Specialty Pharmacy | 09/24/2010 | 09/24/2010 | APPROVED |
| 1234568092 | remi jones | MELISSA MD | 201-111-1234 | REMICADE | 713.00 - 714.2, 714.4 - 714.9 Rheumatoid Arthritis | NuFACTOR Specialty Pharmacy | 09/24/2010 | 09/24/2010 | APPROVED |
| 1234567893 | remi jones | MELISSA MD | 201-111-1234 | PEGASYS | 070.44 -- Chronic hepatitis C with hepatic coma | NuFACTOR Specialty Pharmacy | 09/24/2010 | 09/24/2010 | APPROVED |
| 1234567892 | remi jones | MELISSA MD | 201-111-1234 | PEGASYS | 070.44 -- Chronic hepatitis C with hepatic coma | NuFACTOR Specialty Pharmacy | 09/20/2010 | 09/20/2010 | PENDING |
| 1234567891 | remi jones | MELISSA MD | 201-111-1234 | PEGASYS | 070.44 -- Chronic hepatitis C with hepatic coma | NuFACTOR Specialty Pharmacy | 09/20/2010 | 09/20/2010 | APPROVED |
| 1234567890 | remi jones | MELISSA MD | 201-111-1234 | PEGASYS | 070.44 -- Chronic hepatitis C with hepatic coma | NuFACTOR Specialty Pharmacy | 09/20/2010 | 09/20/2010 | INCOMPLETE |
| 123456780 | remi jones | MELISSA MD | 201-111-1234 | EPOGEN | 285.3 -- Anemia associated with anticancer chemotherapy | SPINSTAR PHARMACY | 08/25/2010 | 08/25/2010 | PENDING |

Authorization Status

Filter records: All
Authorization: Select  Show

| Auth ID# | Patient Name | Prescriber Name | Drug | Diagnosis Code | Pharmacy | Date of Service | Status | Review |
|---|---|---|---|---|---|---|---|---|
| 1234568095 | REMI JONES | NADGE MD | REMICADE | 555.0 - 555.9: Crohn's disease | NuFACTOR Specialty Pharmacy | 12/22/2010 | APPROVED | Review |
| 1234567815 | remi JONES | NADGE MD | OCTAGAM | 279.04 - 279.2: Primary immunodeficiency | NuFACTOR Specialty Pharmacy | 12/21/2010 | APPROVED | Review |
| 1234567814 | David Octagam | NADGE MD | OCTAGAM | 042: Pediatric HIV type 1 infection | NuFACTOR Specialty Pharmacy | 12/15/2010 | APPROVED | Review |
| 1234568094 | Remi jones | MELISSA MD | REMICADE | 555.0 - 555.9: Crohn's disease | NuFACTOR Specialty Pharmacy | 10/01/2010 | PENDING | Review |
| 1234567895 | remi jones | MELISSA MD | PEGASYS | 070.44 -- Chronic hepatitis C with hepatic coma | NuFACTOR Specialty Pharmacy | 10/01/2010 | APPROVED | Review |
| 1234567894 | remi jones | MELISSA MD | PEGASYS | 070.44 -- Chronic hepatitis C with hepatic coma | NuFACTOR Specialty Pharmacy | 10/01/2010 | APPROVED | Review |
| 1234568093 | remi jones | MELISSA MD | REMICADE | 713.00 - 714.2, 714.4 - 714.9: Rheumatoid Arthritis | NuFACTOR Specialty Pharmacy | 09/24/2010 | APPROVED | Review |
| 1234568092 | remi jones | MELISSA MD | REMICADE | 713.00 - 714.2, 714.4 - 714.9: Rheumatoid Arthritis | NuFACTOR Specialty Pharmacy | 09/24/2010 | APPROVED | Review |
| 1234567893 | remi jones | MELISSA MD | PEGASYS | 070.44 -- Chronic hepatitis C with hepatic coma | NuFACTOR Specialty Pharmacy | 09/24/2010 | APPROVED | Review |
| 1234567892 | remi jones | MELISSA MD | PEGASYS | 070.44 -- Chronic hepatitis C with hepatic coma | NuFACTOR Specialty Pharmacy | 09/24/2010 | PENDING | Review |

PROSPECTIVE MANAGEMENT SYSTEM FOR MEDICAL BENEFIT PRESCRIPTIONS

CROSS-REFERENCE TO RELATED APPLICATIONS

This application claims priority from U.S. Provisional Patent Application No. 61/334,242 filed on May 13, 2010.

STATEMENT REGARDING FEDERALLY SPONSORED RESEARCH

Not Applicable.

APPENDIX

Not Applicable.

BACKGROUND OF THE INVENTION

Field of the Invention

The present invention relates to methods and systems for managing the ordering, approving, and filling of biotech/specialty drug prescriptions electronically. In particular, this invention relates to methods and systems in which healthcare providers submit prior authorization requests to health plans, obtain necessary approval per the health plan's approval criteria, and submit medically-coded drug orders to specialty pharmacies, all within a web-enabled platform.

Related Art

Pharmaceuticals come in oral, injected, inhaled, or infused versions. Generally speaking, drugs that are orally ingested or are self-administered are covered under the patients' pharmacy benefit with their respective health insurance plans. Pharmacy Benefit Managers (PBM) prospectively administer each prescription using a drug's National Drug Code (NDC). Every pharmaceutical has an assigned NDC code which describes the package size (number of pills per package) and medication dosages (i.e. mg/pill). While the vast majority of prescriptions are supplied to patients under their pharmacy benefits (approximately 80%), medically coded drugs that require professional administration (i.e. infused, injected, or specific oral medications) are adjudicated as part of a patient's medical benefit portion of their health insurance coverage.

These medically coded medications that fall under the medical benefit tend to be biotech/specialty medications. The "specialty" term as used herein may refer to a drug ("specialty drug" or "specialty medication") or to a pharmacy ("specialty pharmacy"). Specialty drugs are usually made by a biotech manufacturing process, and specialty pharmacies store and dispense these drugs in a manner appropriate for such biotech medications. Generally, a biotech manufacturing process refers to any manufacturing process for the production of medications that have a "biologic" or "protein-based" chemical make-up. These types of medications require injections or infusions rather than being orally ingested as well as special handling/refrigeration, and exhibit toxicities and side-effects which typically necessitate clinical oversight during the course of the prescribed therapy. Drugs produced by biotech manufacturing processes are used to treat a variety of diseases, including cancer.

These specialty drugs require professional administration and/or clinical oversight due to their particular characteristics. Therefore, these medically coded medications are billed manually on the same claim forms that are used for medical procedures, such as the HCFA-1500 or CMS-1500. Medical benefit procedural codes include J, S, and R codes that are used to bill for a drug or other biological that is administered to the patient by a physician (or a properly trained and supervised physician assistant or nurse in the healthcare/medical service provider's office/practice). An example of a current claim form for medical diagnoses, procedures and products, including medically-coded drugs, is shown in FIG. 12. The NDC code is rarely included on the HCFA-1500 form. Currently, HCFA 1500 and CMS 1500 forms do not capture a drug's NDC number to identify vial size, vial strength, or brand of medication dispensed. Manual auditing processes using these forms have been used to capture NDC number dispensed. Accordingly, all of the current processes for using these forms are retrospective (i.e., after the physician has performed the procedure and administered the drug to the patient), and there are no automated prospective systems or processes in place for concurrently verifying patient's eligibility for the drug, controlling the amount of drug that is used, steering to the optimal setting of care, and for controlling duration of therapy before the procedure takes place.

The healthcare providers must continue to use the manual systems and processes for their billing of the medically-coded drugs because, prior to this invention, none of the current systems, including the electronic platforms offered by the PBMs, have appreciated that an integrated system is necessary to automate the process. Specifically, an automated system for ordering medically-coded drugs should have an integrated knowledge-base system that can prospectively evaluate the health plan's requirements for prior authorizations of the drugs, preferably in an adaptive and interactive manner, as well as provide a feedback loop which tracks the corresponding drugs that the healthcare providers ordered from the specialty pharmacies and ultimately administered to the patients. The current PBM systems are not satisfactory for handling medically-coded drugs because the process for pharmacy-benefit drugs is linear, and the systems do not have a feedback loop that is integrated between the services provided by the healthcare provider and drugs dispensed by the pharmacy. Additionally, PBMs can only accept orders from a pharmacy holding a licensed and unique pharmacy provider code. Medically-coded drugs originate in the doctor's office, which cannot access PBM systems.

In the typical situation in which a drug is covered under the patient's pharmacy benefit plan, a treating physician examines the patient, renders a diagnosis and prescribes a drug. The patient (or physician/healthcare provider) chooses a pharmacy and upon receipt, the pharmacy dispenses the drug to the physician's practice or to the patient for administration. The physician's medical office bills the health plan for the medical procedure, and any feedback loop on the services between the medical office and the health plan, including the authorization for the services and ultimate payment thereon, is performed entirely apart from the pharmacy's dispensing of the drugs. In fact, the entire process between the physician and the health plan is completely unrelated to any interaction that may follow between the patient's pharmacy and health plan. Whether or not the patient fills the prescription with the pharmacy has no bearing on whether the healthcare provider will get paid because any authorization from the health plan for the medical services provided are wholly unrelated to the drugs that are prescribed and then dispensed by a pharmacy as the pharmacy-benefit drugs are covered under the pharmacy benefit plan. Therefore, the systems that are used to manage the process between a medical office and its patients' health plans are devoid of any feedback from or integrated with information from the patients' pharmacies.

Similarly, the subsequent process between the patient and the pharmacy, including authorizations from the health plan for coverage of the pharmacy-benefit drugs and subsequent payment, is wholly unrelated to the authorization and payment for the medical services. Whether or not a pharmacy is paid by a health plan for a drug it dispenses is wholly unrelated to any payments a medical office may receive for the medical tests a physician performed on the patient in order to render a diagnosis and prescribe the appropriate drug. Accordingly, the current systems developed for PBM processes are focused on the interaction between the patient and the pharmacy and do not provide for much integration between the pharmacy and the healthcare provider.

Due to the lack of integration, functionality, and feedback in the current systems that are used to manage pharmacy benefit plans, current systems are unable to automate the authorization and approval process for medically-coded drugs. Additionally, the current PBM systems fail to incorporate a knowledge-base that should be used to speed the processing of requests for authorization approvals so that the requests can be performed using adaptive and interactive processes, in real-time. None of the current systems are sufficiently integrated to permit the interactive sharing of information between health plans, healthcare providers and specialty pharmacies to permit the feedback necessary to track medically-coded drugs that healthcare providers order from specialty pharmacies and ultimately administer to their patients in their offices. Lastly, current systems cannot accept electronic requests from the physician's practice, which is where an order for a medically-coded drug would originate.

While less than 20% of drug claims are billed as part of the medical benefit portion of a patient's health insurance, the medications in this category are typically very expensive. In general, a monthly oral prescription averages $50 per prescription, while a monthly medically-coded drug averages $1500 per prescription. Additionally, approximately 45%-50% of the drugs in the near-term pharmaceutical pipeline are likely to be medically-coded drugs. Given these facts, and without the solutions offered by the process and system of the present invention, it is understandably why health plans have increasing concern over ways to control the costs of medically coded drugs. The concern is shared by all payers, including health insurance companies, governmental health plans, and employers.

Medications billed to a medical benefit have National Drug Codes (NDC), but they are difficult to capture and quantify as the primary claim form, the HCFA-1500, cannot accept NDC-level coding. For example, a health plan may approve the use of the biotech drug REMICADE® under the current manual processes. However, under the current process, the plan does not know what dosage of REMICADE® is used or how often it is infused when the approval is given. The REMICADE® drug is dispensed in liquid form for infusion based on patient weight and dose/kg needed for that patient. Even though REMICADE® has an assigned NDC, the current processes require that a J-code be identified to approve REMICADE® for the treatment (instead of the NDC) because a health plan will not know what dose of the drug is dispensed until after the specialty pharmacy has provided the drug to the patient and/or physician. In general, health plans do not know what package size or dosage of medication is requested or dispensed when a medication is billed to the medical benefit. This creates difficulty for payers to implement appropriate utilization management tools to control wastage, inappropriate utilization, and avoidable costs associated with medications dispensed and administered under a patient's medical benefit.

Operationally, health plans lack prospective controls to manage costs associated with medically coded drugs billed as procedural J, R, or S codes. As procedural codes they do not identify drug utilization at the NDC level. Even after an authorization is approved for a medical drug regimen, the cost for that transaction can vary greatly and will not become evident until the claim is submitted. As claims are typically submitted 45-60 days after the date of service, payers can do very little to ensure optimal utilization and cost. Therefore, there is no prospective cost containment on the medically-coded drugs, only a retrospective evaluation based on a formal audit. Instead, what is truly needed is a prospective electronic authorization system which can account for the eligibility status of the patient and to adaptively guide a user to enter patient specific criteria, health plan specific criteria, drug specific criteria, site of drug administration, and select a pharmacy to dispense the medically coded drug. Other needs of the health plan are listed below.

As used herein, health plan generally refers to any entity that owns the "risk" for the medical care provided to its members. The health plan term can be used synonymously with "payer" or "health insurer". Health Plans typically require an approval process for procedures and medications deemed to be high-cost or otherwise having the potential to be mismanaged. Biotech/specialty drugs usually require prior authorization, and when such a procedure or medication is required, the physician or other healthcare service provider contacts the Health Plan via telephone or fax to obtain an approval. Using traditional systems that are currently in place, an approval typically takes 24-72 hours to obtain, and requires the transmittal of clinical and financial information. As it will become apparent from the description of the invention provided herein, the inventive system reduces this approval time period from days to minutes. Once approved, the prescription and approval are submitted to a pharmacy for dispensation, and the delivery of the medication is coordinated with the physician and/or the patient for injection/infusion.

A Pharmacy Benefit Manager (PBM) is a service provider that uses a computer database to manage the utilization of common prescription drugs. Requests for common drugs originate at the retail pharmacy, and the PBM electronically verifies the patient's insurance coverage for the drug, and imposes a tiered out-of-pocket cost structure based on the drug that is ordered. PBMs also reimburse the pharmacy for the drugs that are dispensed using a NCPDP claim form. The vast majority of PBM transactions, including reimbursements, are conducted electronically.

Every pharmaceutical approved for sale in the USA has a specific National Drug Code (NDC). The NDCs are typically 11 digits long, and define drug, manufacturer, vial size, and strength. PBM transactions use the NDC for drug management and reimbursement. However, for the reasons provided above, medically coded drugs do not follow typical PBM adjudication because they require professional oversight, and requests for these drugs originate in a medical practice or clinic. The medically coded drugs are those medications that are often infused or injected that are paid from a patient's medical benefit portion of their health insurance coverage. As also explained above, the HCFA 1500/CMS 1500 forms are typically used by healthcare/medical service providers to bill claims to Health Plans for procedures and/or medications. Biotech medications are typically billed using these forms to charge a blended rate for the drug and the infusion/injection procedure. HCFA-1500 forms do not have the ability to capture the NDC for the drug that is administered, nor can these forms be accepted by a PBM. The medical benefit procedural codes (J, S, R-Codes) are the procedural codes used on the HCFA-1500 claim forms by healthcare/medical service providers to garner reimbursements for administering biotech/specialty medications. J-codes are blended codes, including the cost of the drug and the cost to administer the drug.

For the reasons described above, the present systems and processes that are currently in place for medically coded drugs need to be improved for healthcare service providers, health plans and pharmaceutical manufacturers.

The needs of the health plan stakeholders are described above and are also summarized in the Health Plan Needs table below.

Health Plan Needs

Electronic Platform to:
  Verify Member Eligibility
  Create and Transmit accurate Prescriptions and Supportive Data
  Collect data at NDC Level of the Drug, even medically-coded drugs
  Speed Authorizations to the Physician and Dispensing Pharmacy
Prospective Process for:
  Imposing Appropriate-Use Criteria and Clinical Edits
  Imposing Preferred Drugs and Preferred Regimen
  Directing Orders to Contracted/Credentialed Specialty Pharmacies
  Steerage of the infusion to the Preferred Site of Care
Reporting Suite:
  Provide NDC-to-J-Code Crosswalk reports to obtain Rebates
  Reports to Affect Pharmacy & Therapeutic (P&T) Decisions
Clinical Review:
  Manage the complications of Poly-Pharmacy
  Manage Side-Effects and Toxicities
  Manage Adherence and Compliance
  Manage Dosing and Duration of therapy
  Provide Care Alerts to manage Patient Safety
More Efficient Prior Authorization Workflow:
  Reduce Prior Authorization Time for Physicians and Pharmacies
  Reduce Payer Resources needed for Prior Authorization Process
  Reduce Physician Resources needed for Prior Authorization process Pharmaceutical Manufacturers also have unmet needs associated with specialty pharmaceuticals. From a manufacturer perspective, there is no current way to track medically coded drugs for market share analysis, sales incentive compensation, forecasting, or budgeting of resources. Accordingly, the needs of pharmaceutical manufacturer stakeholders are summarized in the Pharmaceutical Manufacturer Needs table below.

Pharmaceutical Manufacturer Needs

NDC level data for market share and sales analysis:
  For specific drug, vial size, and strength
  For diagnosis class
  By geography Lastly, the specialty pharmacy ultimately dispensing the medication also has unmet needs within the current process. Primarily, the pharmacy upon receipt of a prescription, must allocate tremendous resourcing to verify eligibility and obtain an authorization. Any error during this manual process will cause the claim for the service to be rejected. Given the cost of biotech medications, a rejected claim imposes hardship on a pharmacy. The needs of specialty pharmacy stakeholders are summarized in the Specialty Pharmacy Needs table below.

Specialty Pharmacy Needs

Reduce costs to manually verify eligibility and obtain authorization
Reduce write-offs due to unpaid claims
2-3 day turn-around to obtain authorization
Prospective guidance to optimally manage dosing and duration What is needed for healthcare organizations, including healthcare providers, health plans, pharmaceutical manufacturers and specialty pharmacies, is a system and process that prospectively controls medically coded drugs and replaces the inefficient, time-consuming manual process that is currently used. With prospective controls in place, a health plan can apply utilization management tools, include care alerts, recommended dosing based on evidence-based medicine, and streamline workflow processes for physicians, specialty pharmacies, and internal health plan reviewers. Also, with the ability to assign an accurate NDC to medically-coded drugs (J-code billed medications) data analytics can be improved to capture rebates from drug manufacturers. Rebates are retrospective payments made by manufacturers to pharmacies and other drug purchasers based on the ability to affect the drug's market share. Payments are reconciled by the manufacturer using reports supplied by the pharmacy or healthcare service provider quantifying the amount of drug that was used (as defined by the drug's NDC). For the reasons discussed above, the current systems available to healthcare organizations fail to satisfy these needs. The current systems are summarized below.

Most PBMs use computer platforms for managing pharmacy benefit plans, but these current platforms are unsatisfactory for medically-coded drugs. Current PBM systems do not have a knowledge-base that can evaluate medically-coded drug orders relative to the health plan's medical benefit policies. Without a knowledge-base, there would not be any link between a medically-coded drug and the indicated usage under the health plan's policies nor would there be any information on recommended amounts of the drug dosage for a particular patient which could be based on a number of factors, including the course of treatment (initiation or continuation), weight, sex, age and frequency of therapy. Also, the current PBM systems can only accept requests for therapy from a pharmacy with a unique identifier code, and not from a physician's practice from which medically-coded drugs originate.

When it comes to health plan approval systems, the prior authorization programs currently used by health plans do not provide prospective, adaptive, interactive, automated controls that allow the health plans to manage utilization and generate rebates. Instead, the current systems are manual, with healthcare providers using forms on paper or electronic representations that they submit to the health plan via facsimile or e-mail. Prior authorization forms have been adopted by many plans as a remedial solution to apply basic management tools to medically-coded drugs, and an example is shown in FIGS. 13A and 13B. Using prior authorization forms is a manual process requiring intensive work by medical offices and health plans. The process associated with using prior authorization forms is not streamlined; it is time consuming and creates only a few very basic management controls which are mostly retrospective in nature, where true costs are only known after the medication has been dispensed and administered. Implementing a process using prior authorization forms also does not allow a health plan to determine what NDC should be assigned to a medication dispensed and billed to a patient's medical benefit. Using the current systems typically takes days to process a request for authorization approval to dispense medically-coded drugs and only provides limited management controls. Instead, what is needed is a system using an adaptive process to request a prior authorization where a medical office can submit only relevant information, interactively and in real-time, taking only minutes, not days, and which give prospective management controls to health plans.

Neither the current PBM systems for drugs covered on as part of a patient's pharmacy benefit nor the health plan systems for medical procedures are satisfactory for managing medically-coded drugs. Additionally, merely combining the features of currently known systems would not result in an optimal solution to the issues discussed above. Even though there are systems that provide an interactive ordering process for pharmacy benefit drugs and there are knowledge-bases which help prevent ordering too much medicine and check for adverse drug interactions for a particular patient, merely combining these features fails to result in an integrated system which provides the medical office with the prior authorization approval in a timely manner or provides the health plan with an interactive ordering and pharmacy feedback loop that provides the necessary information for efficiently collecting information to capture rebates on the medically-coded medicines.

Accordingly, to solve the need by healthcare organizations, a new system and process that prospectively controls medical benefit medications is needed, not one which merely combines features from currently known systems.

SUMMARY OF THE INVENTION

The present invention solves the problems described above by providing a prospective, adaptive, interactive, and integrated knowledge-based ordering process for specialty/biotech pharmaceuticals (medically coded drugs). The knowledge-base of the system is based on the health plan's clinical policies, as well as the eligibility status and the patient's medical benefit coverage with their health insurer. It is applied in an adaptive and interactive manner through a web-enabled software application system which provides a real-time, prospective examination and control over requests for authorization to dispense the medically coded drugs. The system also includes a feedback loop from the pharmacies to provide information on the medicines that have actually been dispensed. The present system results in a faster, more-efficient processing of authorization approval requests that is not possible with the current authorization approval process and results in less waste and greater cost savings that could not be realized by the current ordering systems. And by integrating the approval authorization system with the ordering in a unique way with the dispensing feedback system, the present system results not only in benefits that have not been realized before and were impossible to achieve and are also unexpected when considering each of the known systems in an individual manner or when merely combining the features of these known systems.

In one aspect of the present invention, it is a payer-centric system that offers prospective control over a health plan's specialty/biotech pharmacy costs. This system accommodates all medically-coded drugs, including those used to treat cancer, applying a health plan's clinical policies and edits before a medication is dispensed by a specialty pharmacy, hospital infusion suite, or physicians' practice. This system is automated and adaptive through a web-enabled system, creating efficiencies associated with providing metrics required to create a "clean" and authorized prior authorization request. Once a request is approved, it is transmitted to a pharmacy in the health plan's specialty pharmacy provider network with a unique identification number created by the system or some other authorization code that is unique to the transaction.

In another aspect of the invention, it functions as a medical pharmacy benefit manager that allows a health plan to proactively plan, intervene, and manage specialty/biotech pharmacy spending. Specialty/biotech pharmaceuticals are currently processed using procedural codes (i.e. J-codes) that were not easily handled by a health plan for adjudication (payment and processing) because of the retrospective systems and processes that had been used prior to the creation of this invention. Because medically-coded drugs have a complicated payment process which did not fit in the PBM systems and required manual processing and retrospective analysis under the medical benefit plan, prior to the present invention, they had been poorly managed creating waste, inappropriate utilization, safety concerns, and inefficiency.

In another aspect of the invention, it streamlines the health plan's authorization approval process with an integrated electronic, knowledge-based processing system. It allows a health plan to create preferred drug status and metrics, define length of therapy, collect rebates, and improve patient care through an automated system. Prospective controls allow payers to improve patient outcomes by intervening in a patient's care before a medically-coded drug is dispensed, avoiding harmful drug interactions and poly-pharmacy duplications. Because the invention uses an adaptive intake form that guides users to enter only needed metrics, efficiencies also impact the physician's practice where requests for authorizations originate. This adaptive process and knowledge-based system reduces transaction times for approval, and eases the inputting process with algorithms that are consistent with known prescriptive logic.

Additional features, functionalities and benefits that the present invention provides to payers and healthcare providers are listed below.

Features, Functions & Benefits for Payers & Healthcare Providers

Providers have an electronic authorization system that quickly approves medically billed drugs through an interactive and integrated, knowledge-based system.

Payers have prospective controls to improve patient outcomes, reduce drug interactions, manage poly-pharmacy issues, eliminate waste, and reduce inappropriate medication utilization.

Pharmacies will receive a "clean" referral that has validated patient eligibility and conformance to the health plan's clinical policies.

Health plans can enforce optimal drug dosages for prescribed medications based on patient needs, body weight, lab values, and diagnosis.

Health plans can manage length of therapy/duration to create optimal medical outcomes for patients.

Health plans can access manufacturer rebates with NDC-level utilization data.

Patients are provided with Drug Monographs, disease education, and Compliance Tools to promote empowerment and quality of life.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 3 and 3A-3F are flow charts of the system's overall process and sub-processes.

FIGS. 4-11 are screen shots showing the operation of the system.

Figure 12:
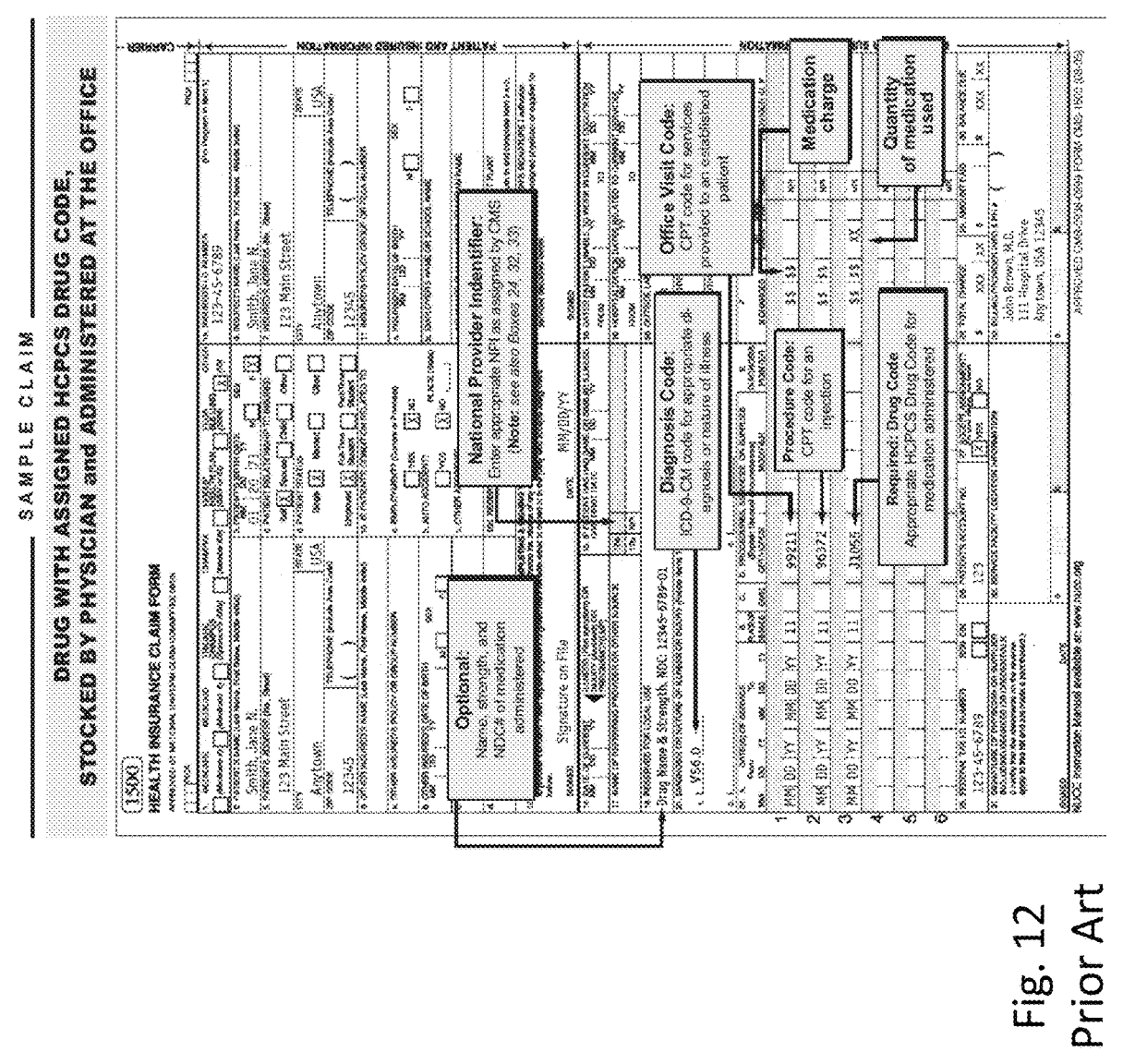

FIG. 12 is a prior art claim form for medical diagnoses, procedures and products.

Figure 13A:
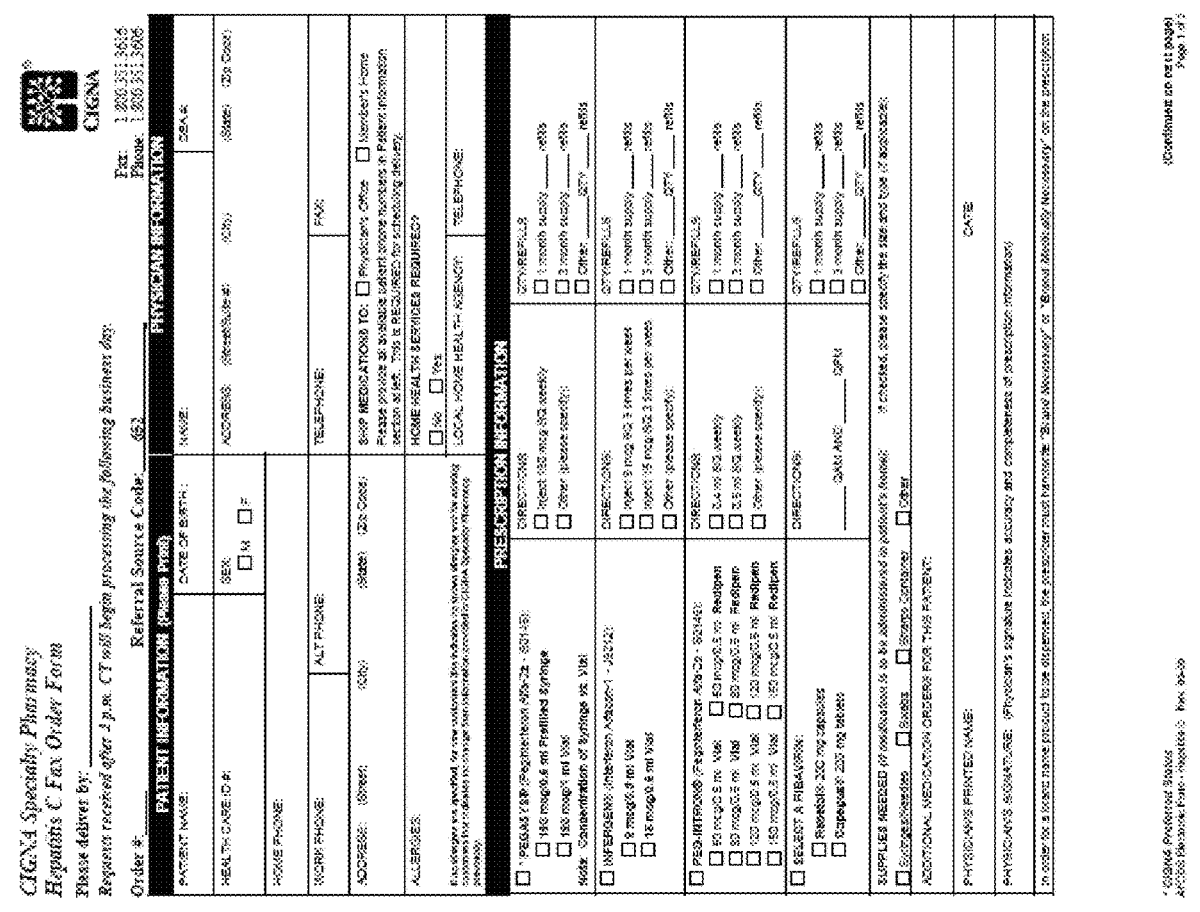
Figure 13B:
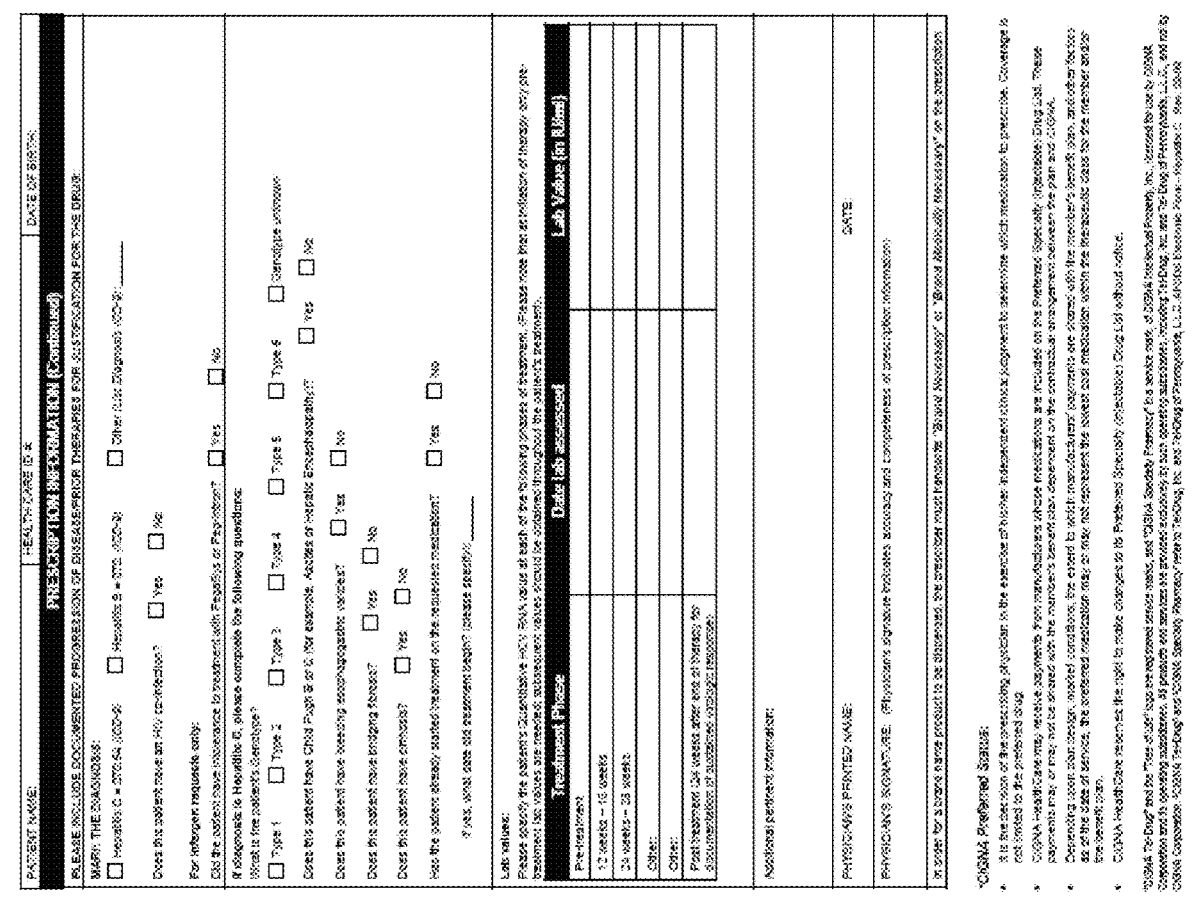

FIG. 13 is a prior art prior authorization form for medically-coded drugs.

DETAILED DESCRIPTION OF THE PREFERRED EMBODIMENTS

The following description of the preferred embodiment(s) is merely exemplary in nature and is in no way intended to limit the invention, its application, or uses.

The present invention, identified by name as the RX Specialty HUB system and process 10, is a software application system intended for direct use by healthcare/medical service providers, health plans, and pharmacies and is preferably web-enabled. The system automates current manual prior authorization processes, applies prospective management controls, and applies NDC-level specificity to medications billed to a medical benefit and not processed through a standard PBM transaction. The system can be used as a stand alone tool or embedded into a physician's electronic medical record software. The inventive system 10 is described below with primary reference to the illustration in FIG. 1. Following the description of the system, the corresponding process and sub-processes of the inventive system 10 are described with reference to the illustrations in FIGS. 1 and 2. Each one of the modules and other features in the system 10 are then particularly described.

System Description

Figure 1:
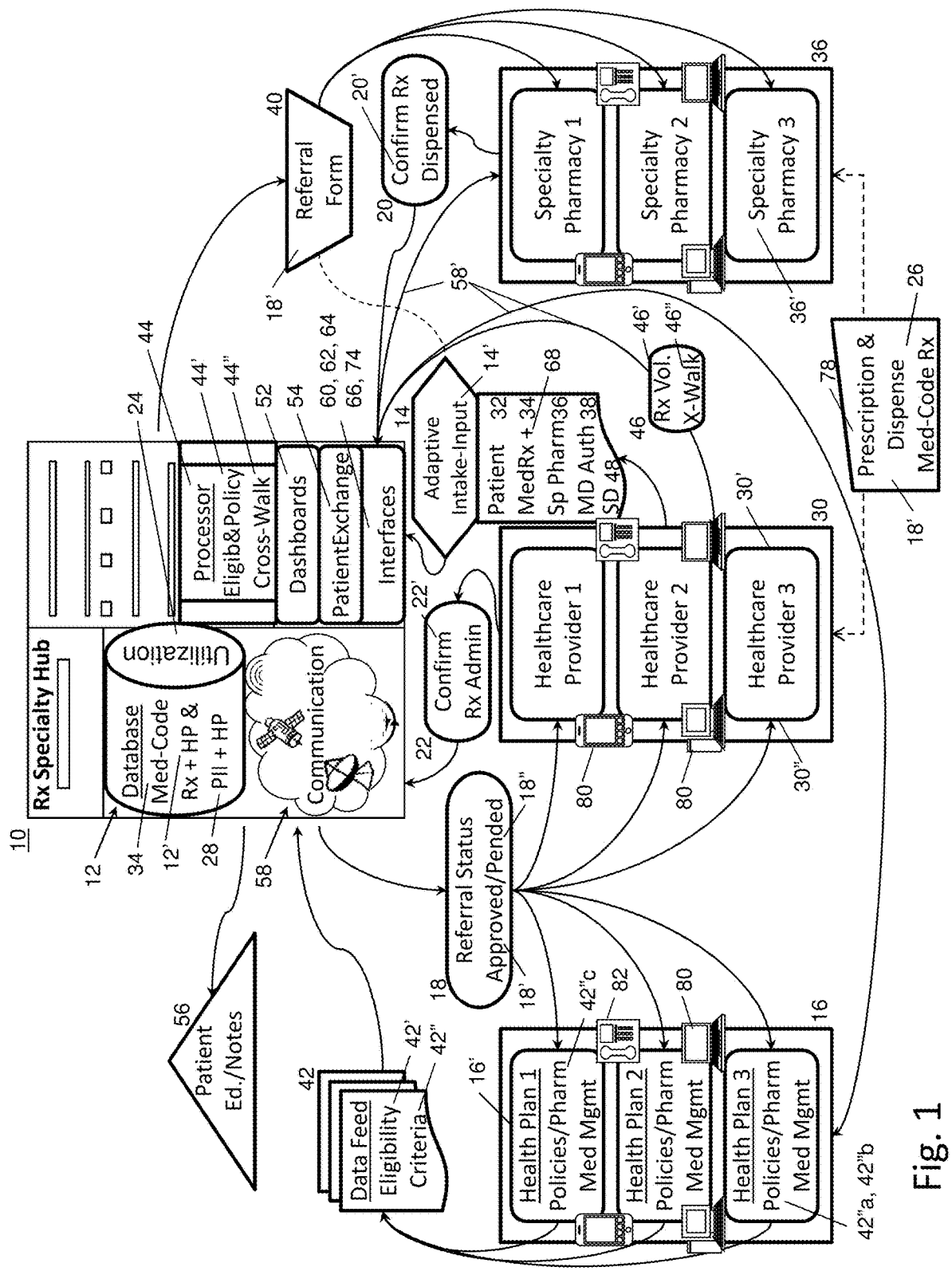
FIG. 1 is a system block diagram of the present invention.

As particularly illustrated by the system block diagram in FIG. 1, the present invention is a medically-coded drug management system and corresponding process 10 which has a database 12 with criteria 12' for a plurality of medically-coded drugs 34 that are associated in the database with a plurality of health plans 16 along with patient identifiable information 28 that is associated with these health plans. The database also contains information on specialty pharmacies 36 with capabilities to dispense the medically-coded drugs 34.

The system has a communication module 58 which allows the database 12 to be in communication with healthcare providers 30 as well as the health plans 16 and the specialty pharmacies 36. The communication module accepts data feeds 42 that are in operative communication between the health plans and the database. Using the data feeds 42, a number of health plans 16 communicate their health plan eligibility data 42' for the patients 32 in the respective health plans to the database 12. The data sets in the data feeds also contain the health plan criteria 42" which, as discussed in detail below, are used to determine whether or not certain medically-coded drugs 34 fit within the health plan guidelines for eligible patients. The communication module 58 also provides for secured communication channels 58' between the system 10 and the health plans 16, the healthcare providers 30 and the specialty pharmacies 36.

The system 10 provides the healthcare providers 30 with a healthcare provider interface 60 with a login interface 62, a data input and review interface 64, and an authorization interface 66. A user 30' who is an authorized representative of a healthcare provider 30 gains access to the system 10 through the login interface 62, submits input data 14' to and accesses stored data 12',28, 34 in the database through the data input and review interface 64 whereby the input data 14' identifies a patient 32' from the entire set of patients 32 using the patient identifiable information 28, and by using an adaptive intake template 14 that is linked to the database 12, the system 10 automatically correlates the patient 32' with a corresponding health plan 16' and completes the remaining data fields 14" in the adaptive intake 14 with information taken from the database based on the user input 14'. For example, the processor 44 may select corresponding patient information, health plan information and/or therapy options from the database according to the user input 14'. The authorized representative 30' can also select a medically-coded drug 34' from the list of medically-coded drugs 34 and can choose a specialty pharmacy 36' from the available specialty pharmacies 36. When an identified patient 32' is approved for a medically-coded drug 34' as a part of a healthcare provider's treatment plan, the authorized representative 30' receives an approved authorization code 18' through the authorization interface 66.

To determine whether or not a patient 32' is approved for a medically-coded drug 34' that has been selected by the healthcare provider's authorized representative 30', the system uses a processor 44 that communicates with the database 12 and the healthcare provider interface 60. The processor 44 executes logic engines 44' with information received form the database and the healthcare provider interface to determine whether the identified patient is verified by the health plan eligibility data. When a patient is verified as being an eligible member of a health plan, the processor 44 produces an authentication code 18 which is a unique transaction with a relational link between the identified patient, the selected medically-coded drug and the authorized healthcare provider.

As discussed in more detail below, when a prior authorization request 38 is submitted into the system 10, if the system's logic engine processing 44' cannot approve the request 38 automatically, the request status 38' may be pended 18" while a medical management reviewer 76 evaluates the details of the prior authorization request 38. In the event that the prior authorization request 38 is approved 18', the request status 38' changes from pended 18" to approved 18' and the overall transaction retains the same authentication code 18. Accordingly, in tracking a transaction through its entire life cycle using the present invention, the system 10 preferably uses an authentication code 18 in combination with an approved status 18' as the transaction's authorization code 18', and the system would have used the same authentication code 18 in combination with a pended status 18" while the authorization request 38 had been pended. It will be appreciated that the present invention could also use an authentication code that has alpha-numeric variations for the pended status and the approved status, such as a suffix-p and a suffix-a respectively used in combination with the authentication code.

Once the transaction is authorized, the healthcare provider's representative 30' can use the system 10 to generate a referral form 40 and select a specialty pharmacy 36' for medication fulfillment, i.e., dispensed medically-coded drugs 26. The healthcare provider may also or alternatively send an electronic prescription 78 directly to a chosen specialty pharmacy 36'. Whichever method the healthcare provider decides to use, the fulfillment continues to be identified and tracked within the system 10 as a part of the same overall transaction with the unique authentication number 18 that was assigned to the transaction when the authorization request was initially submitted.

The system 10 can receive a pharmacy dispensing report 20 through the system 10 from the chosen specialty pharmacy 36'. As discussed above, the pharmacy dispensing report 20 is associated with the authorization code 18' and provides a pharmacy confirmation 20' that the selected medically-coded drug 34' was dispensed 26 to the authorized healthcare provider 30'. As discussed below with respect to the J-Code/NDC cross-walk process 44", the pharmacy confirmation 20' includes a dosing detail 50 at the NDC level. To complete the transaction, the system receives a medical claims report 22 from the authorized healthcare provider 30'. As with the pharmacy dispensing report and all other aspects of the overall transaction, the medical claims report 22 is associated with the same authorization code 18' and provides a medical confirmation 22' that the selected medically-coded drug 34' was administered to the particularly identified patient 32'. Once the feedback is received from healthcare provider that the medically-coded drug has been administered and the transaction is completed, the processor 44 calculates utilization data 24 corresponding to the pharmacy dispensing report and the medical claims report and updates the utilization data in the database.

In the preferred embodiment, the healthcare provider interface 60 is implemented in a computer network 80, which may include any computer having a display screen, particularly including smart phones. It will also be appreciated that the healthcare provider interface could be implemented in a telephony network 82. In the preferred computer system configuration, the login interface 62 is a web-enabled login screen 62' whereas in the telephonic arrangement, the login interface 62 can be implemented using a telephonic keypad-entry login prompt 62". Similarly, the data input and review interface 64 can be a web-enabled data screen 64' or a telephonic keypad-entry data prompt 64"*a* with a telephonic headset data report 64"*b*, and the authorization interface 66 can be a web-enabled authorization screen 66' and a telephonic headset authorization report 66". Accordingly, the secured communication channel 58' can be a web-enabled communication link, a telephonic communication link or any other type of electronic communication system, including satellite, WiFi or cable.

When the system 10 is implemented in a computer network 80, the processor 44 and the web-enabled data screen 64' produces the adaptive intake form 14. Similarly, when the system is implemented in a telephony network 82, the processor 44 and the telephonic keypad-entry data prompt 64"*a* and the information provided orally in the telephonic headset data report 64"*b* is stored in the database 12 as the adaptive intake form 14. Regardless of the particular implementation of the system, computer network or telephony network, the adaptive intake form 14 is based on patient specific metrics 32 and drug specific criteria 34 that the processor 44 uses to retrieve information from the database and automatically complete the fields in the adaptive intake form. Accordingly, with the automatic completion of the adaptive intake form 14, only the required inputs are prompted for the user to enter. The adaptive intake form 14 is used to generate the referral form 40 that corresponds to the healthcare provider 30' and the chosen specialty pharmacy 36'.

The system 10 provides the healthcare providers, health plans and specialty pharmacies with dashboards 52 for tracking and managing the medically-coded drug transactions with which they are associated (i.e., a healthcare provider dashboard 52*a*, a health plan dashboard 52*b* and a specialty pharmacy dashboard 52*c*). Accordingly, each one of the dashboards 52 has a respective docket 52' that summarizes the information from the database 12. The docket 52' in the healthcare provider dashboard includes an authorization request docket having a status report with a tracking of approved and pending authorization requests and an identification of pending tasks for completion. The health plan dashboard's docket has a store of prior authorization requests, a viewer of the completed intake forms and clinical policies corresponding with the particular health plan, a task tracker and a medical management review interface 74. The specialty pharmacy dashboard has a report of approved requests tasked to the pharmacy for dispensation with a status of said request according to a need-by date. The system 10 also provides an efficient way for health plans and healthcare providers to communicate patient information and educational materials 56 with each other and with their respective insureds and patients through a patient exchange 54.

Operation of System

Figure 2:
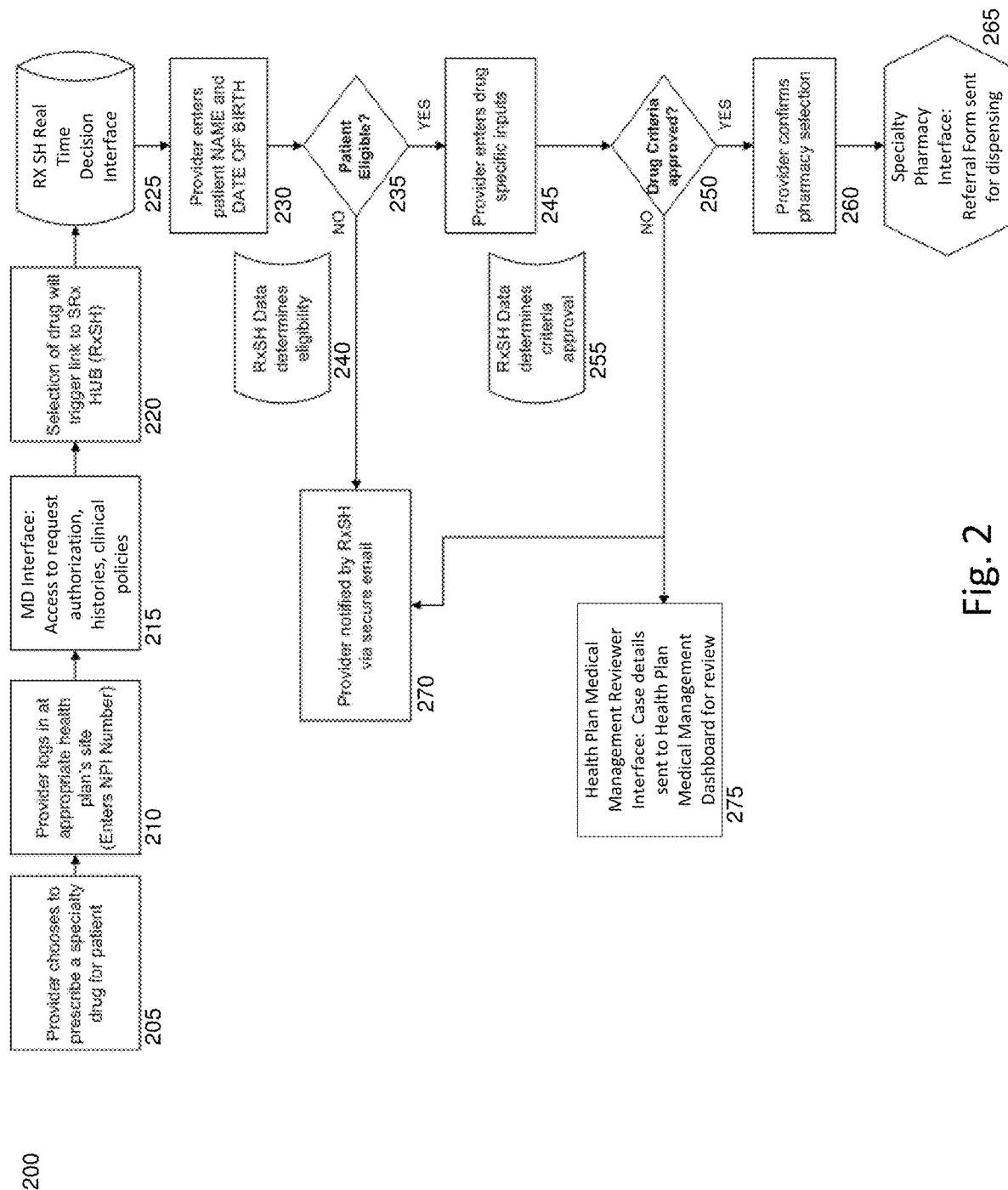
FIG. 2 is a flow chart of the system's process from the perspective of a healthcare provider.

The operation of the system, as described below, is particularly illustrated in the corresponding illustrations from the perspective of a healthcare provider user 30' in FIG. 2 and from the perspective of the system 10 in FIGS. 3 and 3A-3F.

From the user's viewpoint 200, the healthcare provider chooses to prescribe a medically-coded drug (specialty drug) for a patient 205. The user 30' logs into the system 10 and authenticates their user rights to access the system through the login interface 62 as an authorized representative of the healthcare provider 210. It will be appreciated that the system may be implemented as a centralized system for multiple health plans or it may be implemented by a number of individual health plans.

The user accesses the database 12 through the healthcare provider interface 60 and selects the desired medically-coded drug from the list of specialty drugs 215. The selection of the drug triggers a link between adaptive intake 14 and the pharmacy benefit management database 220. With the database link established 225, the user 30' enters the patient's name and date of birth 230. As discussed above, with the link between the adaptive intake 14 and the database 12, the processor is able to automatically retrieve the other information for the identified patient 32' to complete the inputs 14'. As discussed in more detail below, the system's processor then determines whether the patient is eligible 235, 240. For an eligible patient, the user enters drug specific inputs 245 and the system determines whether the therapy criteria 72 meets with the health plan policies 250, 255. When the criteria is approved, the user confirms the selection of a specialty pharmacy 260 and the authorization code is sent to the selected specialty pharmacy for dispensing the medically-coded drug 265.

The automation provided by the system 10 makes the entire authorization process much more efficient and timely so that the authorization code 18' is typically received within ten (10) minutes after entering the authorization request. The authorization code can be received in real-time, nearly instantaneously after the authorization request is entered while the user remains logged in with authenticated user rights and is accessing the healthcare provider interface.

In the event that the patient is not eligible, the healthcare provider is notified by the system 270. In the event that the drug criteria is pended, the case details are sent to the health plan's medical management reviewer for further investigation 275. As discussed above, the medical management reviewer may authorize or deny the medically-coded drug as covered or not covered by the patient's health plan medical benefit, respectively. The medical manager reviewer may also require additional information from the healthcare provider in order to make a determination on the transaction's prior authorization request. Accordingly, the healthcare provider user may send supporting documentation (SD) 48 to demonstrate a justified use of the medically-coded drug with a particular patient that may have otherwise been outside said clinical policies in the health plan. In this way, the pending medical management decision allows for an exchange of information between the healthcare provider and the health plan regarding the recommended therapy and health plan policies for the particular patient.

When the medically-coded drug is authorized, the healthcare provider (or possibly the patient) receives the selected medically-coded drug from the chosen specialty pharmacy or the healthcare provider purchases the medically-coded drug. The healthcare provider administers the selected medically-coded drug to the patient. The specialty pharmacy or healthcare provider submits the medical claims report 22 to the system 10 which stores it within the database 12. As discussed above, the medical claims report is linked to the entire transaction through the authorization code and adds a medical confirmation 22' that the selected medically-coded drug 34' was dispensed 26 administered to said identified patient.

The process is repeated numerous times for many different types of medically-coded drugs and corresponding patients. After the process is repeated for a period of time, the system sends a drug level report 46 summarizing the volumes 46' of the medically-coded drugs administered to the patients. The report can also contain a cross-walk key 46" correlating the medically-coded drugs with corresponding prescription drug codes.

The system's viewpoint of the process 300 is similar to the viewpoint of the healthcare provider user 30' but with much greater detail of the behind-the-scenes processing to make the system 10 function efficiently. Also, the system 10 provides additional functionality for the health plan users, particularly including the medical management reviewers, and for the specialty pharmacy users which is not readily apparent from the healthcare provider user's perspective.

As described above, the database 12 periodically receives data feeds 42 from the health plans 16. The data feeds include a patient eligibility information data feed 42', patient identifiable information associated with the respective health plans, and a clinical policy data feed 42". The system 10 interactively receives an input 14' from a healthcare provider user 30' through the healthcare provider interface 60 in which a health plan is selected 14a, a medically-coded drug is selected 14b, and a particular patient is identified 14c. The logic engines 44' of the system's processor 44 checks the patient information with the patient information and health plan information in the database to determine the eligibility of the patient 305. When the patient is eligible, the system automatically correlates the patient 32' with a corresponding health plan 16' and completes the remaining data fields 14" in the adaptive intake 14 with information taken from the database based on the user input 310.

The physician enters the weight and/or body mass of the patient and the diagnosis code 70 (ICD-9) 315. The logic engines 44' of the system's processor 44 determine whether the patient meets the corresponding set of clinical policies in the patient's health plan 320. The intake form is adaptive based on the patient weight, body mass and diagnosis code such that diagnostic feeds auto-populate the inputs when they are available 325. The healthcare provider user 30' enters the remaining patient clinical values and site of care 30" needs 330. The system 10 then determines whether the patient's clinical status and site of care requirements meet with other sets of clinical policies in the patient's health plan 335. The intake form adapts based on the health plan dispensing criteria and the drug dispensing options 340. The healthcare provider user can use the healthcare provider interface 60 and choose either to purchase the medically-coded drug or use a specialty pharmacy 345. The system again determines whether the chosen specialty pharmacy meets with a set of acceptable dispensing options in the health plan 350. In the event that the healthcare provider would prefer to purchase the medically-coded drug using a "Buy and Bill" model, the healthcare provider is identified as the specialty pharmacy.

In the event that the patient is not eligible under their health plan, the system notifies the healthcare provider accordingly 355. In the event that the patient's diagnosis, clinical status or site of care does not meet the health plan's corresponding set of clinical policies, or in the event that the dispensing choice does not meet the corresponding health plan policy, the healthcare provider is notified of the pending medical management decision 360, and the pended prior authorization request is docketed in the medical management reviewer dashboard 52b for viewing and entering a disposition.

When the patient diagnosis, clinical status and site of care meet the health plan's corresponding set of clinical policies and the dispensing choice also meets the corresponding health plan policy, or when the medical management reviewer approves a pended prior authorization request, the system provides an approved authorization code 18' to the user 365. As discussed above, the authorization code is a unique transaction identifier between the healthcare provider and the identified patient for the selected medically-coded drug 34' and therapy criteria 72 with the therapy criteria 72 being a duration period 72' and/or a dosage level 72". Again, as described above, the adaptive intake template form 14 is converted into a specialty pharmacy referral form 40 that the system 10 reports to the chosen specialty pharmacy 36' or the user sends to the chosen specialty pharmacy 36' an e-prescription with the authorization code 375.

After the chosen specialty pharmacy 36' dispenses the medically-coded drug 34, the specialty pharmacy 36' sends and the system 10 receives a pharmacy dispensing report 20. The dispensing report 20 is associated with said authorization code and provides a pharmacy confirmation that the selected medically-coded drug was dispensed to the healthcare provider or the identified patient. As discussed below with respect to the J-Code/NDC cross-walk process 44", the pharmacy confirmation 20' includes a dosing detail 50 at the NDC level 380. The system also receives a medical claims report from the health plan. The medical claims report is associated with the authorization code and provides a medical confirmation that the selected medically-coded drug was administered to the identified patient at the approved dosage. The database 12 is updated with utilization data corresponding to the pharmacy dispensing report and the medical claims report.

The system 10 accumulates the utilization data from a number of pharmacy dispensing reports for a particular health plan and/or healthcare provider. The system can prepare a utilization report from the accumulated data which the health plan can use to reconcile rebate amounts.

The main features and functions are summarized in the list below and further supported by the corresponding illustrations, including block diagrams, flow charts and screen shots of the interactive interface envisioned for the RX Specialty HUB system.

Web-Enabled Software Application—Features & Functions

Real time prior authorization approval using an adaptive process specific to health plan policies, prescriber needs, and patient eligibility Formulary management of Specialty/Biotech Drugs leading to cost management and rebate generation opportunities Drug dosing calculators and other drug specific deterministic criteria based on ICD-9 diagnosis, initiation or continuation of therapy, FDA recommendations, and industry/evidence based guidelines MD, Health Plan Medical Management, and Specialty Pharmacy "Dashboards" to view all submitted requests, the submission date, and status of the request Clinical Parameters (lab values and other clinical metrics), Site of Care for Medication Administration, and Medication Dispensing information captured and reported to the health plan Care alerts reminding prescribers of precautions needed with usage or administration of medication during the prescriptive process Monitoring capabilities to manage appropriate duration of therapy and discontinuation of ineffective medication (includes lab value monitoring, Quality of Life monitoring, and other efficacy metrics)

E-prescribing capabilities (as technologies become entrenched)

Connectivity to, and automated transactions to find relevant clinical data in a patient's electronic medical records (EMR) when they become widely-established Ability to transmit educational materials, Compliance Reminders, and other supportive documents to a patient's email address NDC assigned to all medically coded drugs dispensed as part of a medical benefit HIPPA compliant data management Secure and redundant data storage Drug-specific market share and utilization data Complete patient information provided for Medical Management Review when parameters are outside of clinical policies E-mail notification of reminders to healthcare provider and medical management reviewers about the status of the medication request Consistent referral forms generated for approved request and provided in real time to Specialty Pharmacies for drug fulfillment. Provided via facsimile, e-mail, or web-based mediums Reduced non-approved experimental use of medications Uploading of support documentation (reports, lab values, pictures, MRIs, etc.) as justification to use medications in patients that are outside of clinical parameters Referring again to the block diagram of the RX Specialty HUB system 10 in FIG. 1, there are several key interfaces designed specifically for use by the healthcare/medical service provider (physician, nurse and their medical office staff), the specialty pharmacy and pharmacist, and the overseers and reviewers at the health plan. These interfaces are accessible via a standard web browser after the user has been successfully authenticated to the system.

RX Specialty HUB uses the database 12 at its core, serving a variety of web interfaces. It is constantly processing data inputs through its logic engines, creating an adaptive intake form to guide the user through a branching logic process for adjudication of a medically coded drug requiring prior authorization approval. The database contains many groups of tables, each with parent to child relationships, main examples of which are: Patient Eligibility Tables, Drug Tables, Pharmacy Tables, and Prescriber Tables. As it is a transactional framework, query-based algorithms are coded behind the web-based user interfaces. This allows for processing of healthcare provider or health plan Medical Management inputs against pre-approval authorized rules from the health plan. As some rules are dependent on prior inputs, the logic is branched and/or nested so as to provide a final adjudication on the authorization request.

Data elements can be entered into the system by the healthcare provider and the health plan through prompted drop-down and radio button selections. Data elements required to substantiate approvals can also be auto-populated via access with patients' electronic medical records (EMR) and other clinical data inputs. The healthcare provider can generate a referral form and select a specialty pharmacy for medication fulfillment and can also send an electronic prescription directly to a chosen specialty pharmacy. As generally referred to herein, electronic medical records (EMR) refer to any system or process where a patient's entire health history and records are catalogued in a standardized format or manner and housed in a secure and searchable database to provide real-time information for medical decision-making.

Patient data is either directly input into RX Specialty HUB by a professional healthcare provider (nurse, physician, physician assistant, or pharmacist), called into RX Specialty HUB telephonically and input by a RX Specialty HUB specialist or customer service representative, or via electronic access to the patient's Electronic Medical Record. Clinical rules to process inputs are coded directly into the RX Specialty Hub application using application programming statements, generating an adaptive intake form which guides users to input only specific metrics. Eligibility Files are integrated directly into RX Specialty HUB through either a direct connection with a health plan, through secure FTP or through another HIPAA compliant and secure data transfer process. Inputs captured in the adaptive intake form are used to generate a referral form with the same unique authorization code 18 that is consistently used throughout the transaction in the Rx Specialty Hub system with the healthcare provider, the health plan and the specialty pharmacy. Healthcare providers can send this referral form through the Rx Specialty Hub system to a selected specialty pharmacy for fulfillment of the medication; or healthcare providers can send an electronic prescription directly to a chosen specialty pharmacy. Electronic prescribing uses data transfer mechanisms required by e-prescribing laws. Referral forms are generated within RX Specialty HUB and e-mailed, faxed, or uploaded to a secure website for use by specialty pharmacies to fulfill medication requests. Physicians who are purchasing the medically-coded drugs are identified as specialty pharmacies. Specialty pharmacies use SMTP (email), FTP or an alternative secure electronic transfer process to provide feedback to the RX Specialty HUB system on all medication dispensed using RX Specialty HUB's referral process. The claims that are paid by the health plan are also electronically submitted to RX Specialty HUB.

Figure 3:
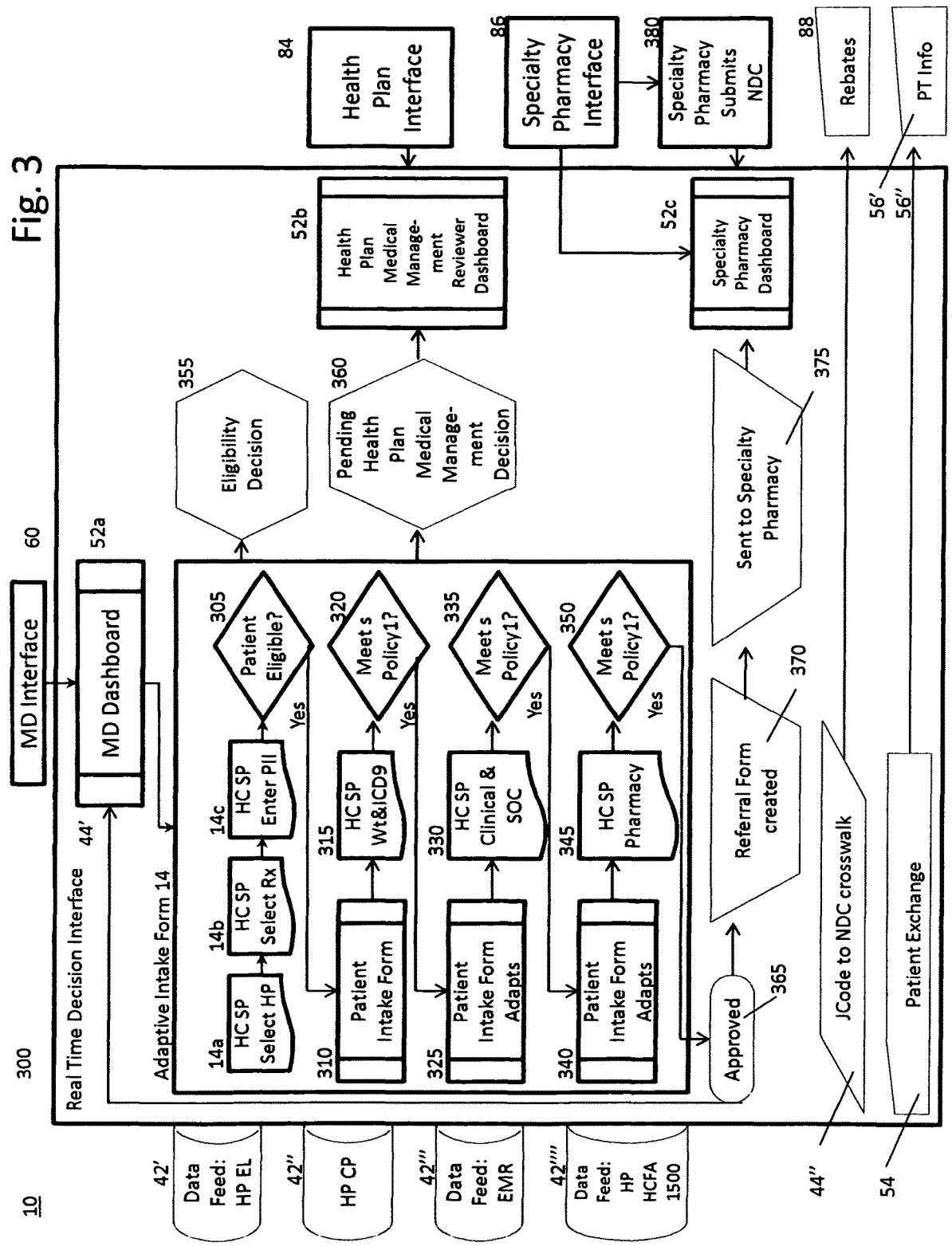
Figure 3C:
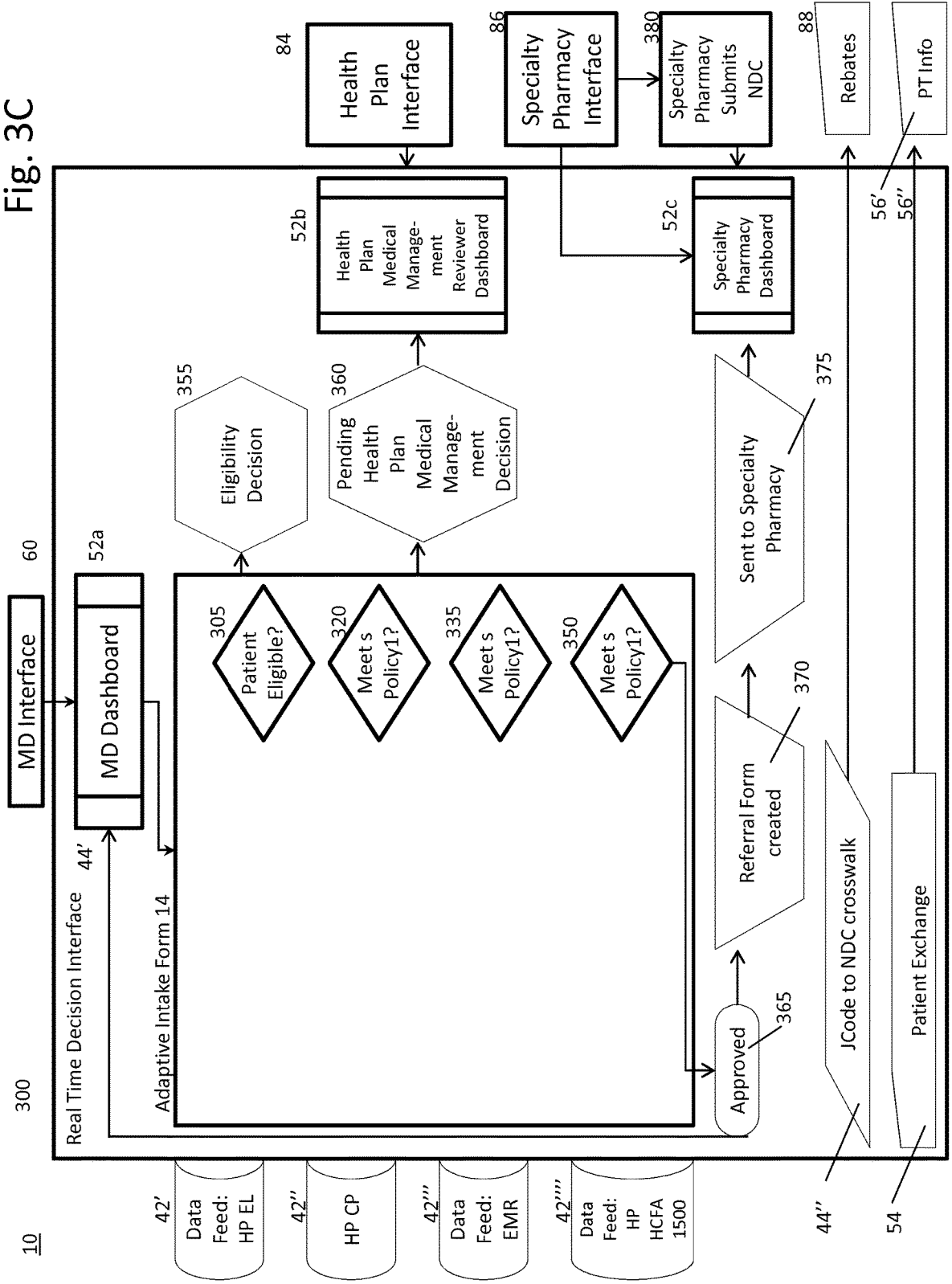
Figure 3F:
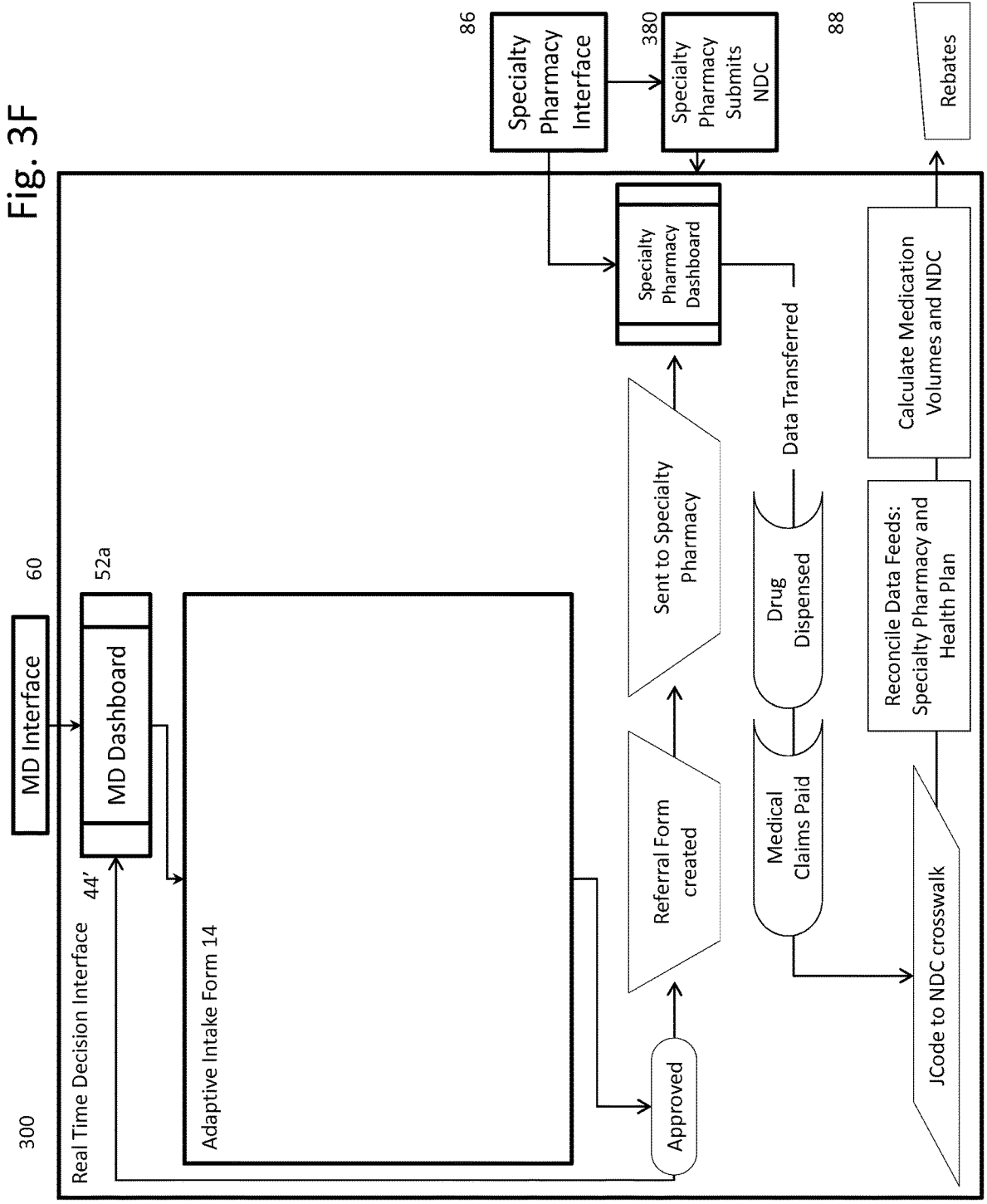

Several processes that comprise the RX Specialty HUB system are described below, including the MD Workflow and Process Overview as illustrated in the flow chart of FIG. 2, the Overall Process as illustrated in FIG. 3 and particularly described with reference to the MD Interface, the Specialty Pharmacy Interface, the Data Feeds, the Real-Time Decision Interface, the Does Not Meet Criteria-Pending Medical Review Notifications and Approval Notifications and the J-Code/NDC Conversion Cross-Walk in the corresponding detail drawings.

MD Workflow and Process Overview

Once a physician diagnoses a condition and determines the appropriate medication for treating the condition, the current healthcare provider's medication-prescribing workflow requires them to determine specifically if that patient is actively covered by the described health plan. Then, the physician must determine if the medication is dispensed through a retail or specialty pharmacy and if the medication should be billed to the patient's medical benefit portion of their health insurance. The physician will then determine if a prior authorization is necessary before the medication can be filled. If a prior authorization is needed under the current process, the healthcare provider must find a prior authorization form (either a hard copy or an electronic version), and then complete and submit the written form via facsimile or e-mail to the health plan. These drug specific forms may be located online or the healthcare provider may need to request a prior authorization form from the health plan which may be faxed, e-mailed or mailed by a postal carrier. Once a prior authorization form is located, the healthcare provider must review the health plan's clinical policy to determine the required information because there is little consistency in prior authorization forms among health plans. The healthcare provider then enters patient specific criteria on the prior authorization form used by a health plan.

Patient specific criteria entered on the form may include patient contact information, birthday, age, weight, specific disease-related parameters and lab results. This information is usually gathered from a patient's file or found in an EMR and manually written onto the prior authorization form. Once a prior authorization form is filled out, usually by a nurse or trained medical office staff, it is faxed back to the health plan for review by their medical management department.

Upon receipt of the form by the health plan, each prior authorization form is manually reviewed by a health plan's medical management staff reviewer and either approved or not-approved based on clinical policies and other guidelines that the health plan has implemented and are within the policy of the particular patient's care that is the subject of the transaction and is being evaluated. During the evaluation process, a medical management reviewer may contact the healthcare provider for additional information not shown on the form. This back and forth data collection process could take between 2-5 days, depending on the schedules and availability of the reviewer and the healthcare provider and the data being sought, including the availability of patient data.

The RX Specialty Hub system significantly improves a healthcare provider's workflow to reduce the time associated with filling out a prior authorization form and the time required to determine if a prior authorization has been approved. The time to approve a prior authorization request (MD Auth) using the RX Specialty HUB is typically less than 5-10 minutes depending on the complexity of the medication. When a physician determines the appropriate medication, he/she logs into the web-based system and chooses the appropriate medication. Each medication has specific clinical, site of care, and dispensing inputs based on its ICD-9 diagnosis code and whether a patient is initiating or continuing therapy. In general, ICD-9 codes reflect the diagnosis determined by the physician upon patient examination, and are specific to a disease, and even to a certain stage of the disease. Because an adaptive intake form is used as part of the Real Time Decision Interface, all required metrics are efficiently captured prospectively, before a prescription is dispensed and administered.

Because patients may have variations in coverage associated with medications provided as part of their medical benefit, healthcare providers are prompted to enter patient insurance information. This information is captured and validated by the RX Specialty Hub Real Time Decision Interface with insurance eligibility information provided from the patient's health plan.

Healthcare providers are prompted to enter information as efficiently as possible, leveraging drop down boxes and/or simple radio buttons wherever possible. An adaptive form is used for required inputs, minimizing the use of free text fields, which results in communication between a healthcare provider and reviewer being more accurate and streamlined than the traditional manual process, and input time is reduced. Also, the approval parameters are asked prospectively, which means that no additional information needs to be collected if a patient is within clinical parameters for using the medication. If a patient is within clinical parameters, a prior authorization is automatically approved and an RX Specialty HUB authorization number, or some other unique transaction-specific authorization code, is automatically generated when a healthcare provider clicks on the "final submit" button. Past and current referral requests are tracked and viewable by the physician on the MD Dashboard, with referral status (approved or pended) clearly designated for each unique referral request and corresponding authorization codes for approved referrals. The MD Dashboard allows for a direct viewing of requests and management of the entire workflow.

If a patient does not meet all clinical policy parameters and other guidelines required by a health plan, the prior authorization will remain pended for medical management review and the healthcare provider will be notified that the request does not meet criteria. The healthcare provider can either modify information requested so that it is within clinical parameters, call medical management to discuss why a patient requires unique care, or enter free text "notes" for the reviewer and wait for a reviewer to assess the case. The healthcare/medical service provider can also upload supporting documentation (SD) to justify use of a medication in a patient outside a health plan's clinical policies. Using a "browse-upload" function, electronic physician notes, lab reports, MRI or X-Ray results can be attached and included as part of the authorization sent to the health plan's Medical Management reviewing department.

Once a healthcare provider clicks the "final submit" button, a date/time stamp is applied to the transaction. Whether a patient's prior authorization request is approved or pended, the RX Specialty Hub system reduces the transaction time from 2-5 days to minutes. This improves efficiency for the healthcare provider workflow, increases appropriate utilization of medication, and ultimately improves patient care.

The RX Specialty Hub system improves a health plan's medical management reviewer workflow and lessens the time associated with each prior authorization request. Little time is needed to re-assess these requests because prior authorization requests that meet clinical policy are automatically approved. By using the Health Plan Interface, medical management reviewers have much more consistent and complete information to make quick decisions requiring few additional interactions with healthcare providers because the prior authorization requests that do not meet the clinical policies already include all relevant patient information. As part of the Health Plan Interface, a Health Plan Medical Management Reviewer Dashboard is provided as a home page to track authorization requests.

The RX Specialty Hub system also improves a specialty pharmacy workflow and lessens the time associated with each prior authorization request. Specialty pharmacies are provided with qualified referrals that already meet a health plan's clinical policies. Little additional work is needed to determine if a patient is eligible for therapy and what therapy requirements have been approved. To track referrals and manage workflow, a Specialty Pharmacy Dashboard is provided for specialty pharmacies using the system.

MD Interface (60)

The MD Interface 60 is used by the healthcare provider (physician, nurse, or practice extender) to process a medically-coded drug authorization requests using RX Specialty Hub's Real Time Decision Interface 44'. Access to a web-based application is the preferred method of operation for the RX Specialty HUB system, and it will also be appreciated that a request can be called into RX Specialty Hub and processed by a RX Specialty Hub specialist or customer service representative. Since most of the information is already available through the knowledge base, it will also be appreciated that an automated telephony system could also be used with verbal menu prompts, a secured smart-phone application, or secured text prompts which may be used in combination with a smart-phone application. For medically coded drugs, the MD Interface allows for real-time connectivity to the Health Plan's eligibility files and clinical policies. Once connected, transactions are conducted electronically to reduce turn-around time.

MD Dashboard (52*a*)

After a physician enters RX Specialty Hub via secure authentication, a summary of all previous prior authorization requests is shown as part of the MD Dashboard 52*a*. This dashboard is part of the Real Time Decision Interface and contains a real time summary of data entered with a unique ID used for the authorization requests processed within system. This dashboard serves as a home page or starting point for healthcare providers using the tool. The dashboard shows a summary of all transactions (approved and pended prior authorization requests) entered by that healthcare provider on the system, tracks authorization requests, and identifies additional tasks for completion.

Real Time Decision Interface (44')

The RX Specialty HUB system can process multiple transactions simultaneously. For example, it can be expected that the system will have a transaction rate in the range of between 1 and 4 transactions per second (TPS) arriving via Provider Web-Direct screens. Each request is transformed into a database query to be validated against the two (2) eligibility data sets from the health plan. The output of the Real Time Decision Interface will have one of the two optional results listed below.

1. APPROVED
2. PENDED—Pending Medical Management Review

Patient Eligibility Check results in APPROVE/PENDED where pended notifications are presented back to the healthcare provider in the form of their preference, via e-mail or notification via the same web interface used to submit the request. Requests are tracked in the MD Dashboard.

If the patient eligibility is APPROVED, the specific specialty drug information is cross-referenced regarding the complete form submitted and the RX Specialty Hub system assigns a specific unique authorization number or other authorization code to the transaction. Approvals result in a Specialty Pharmacy Referral Form sent to the chosen specialty pharmacy. Pended or not-approved requests are sent to the health plan's medical management staff for further analysis and review. Healthcare providers are notified that their request is "Pending Medical Management Review." Any decisions or actions based on the health plan's assessment are managed using the system between the health plan, healthcare provider, and pharmacy. Unless a new form is submitted, the process is closed. All requests are tracked and reviewable by the healthcare provider in the MD Dashboard.

Adaptive Intake Form (14)

As part of an authorization request, an adaptive intake form 14 is generated based on patient specific metrics (patient identifiable information—PII) 32, drug specific criteria, and each health plan's clinical policies Ultimately, the inputs are used to determine if patients are within a health plan's clinical policies associated with the criteria listed in the table below.

Health Plan Clinical Policy Criteria

Is the patient eligible (do they have insurance coverage)?

Does the patient's diagnosis meet the health plan's clinical policy criteria?

Do the patient's clinical metrics and will the drug be administered in a site of care 30" that meets the health plan's clinical policies?

Does the drug dispensing choice meet a health plan's clinical policies?

Because the intake form is adaptive based on patient specific metrics (i.e. diagnosis) and drug specific criteria (i.e. drug dose, duration, frequency of administration, and site of administration) only inputs that are required are prompted for users to enter. By minimizing user inputs, this tool creates both administrative efficiencies and more robust data collection to determine if a patient meets a health plan's clinical policies.

Since the RX Specialty Hub system is interactive, it permits the automatic completion of a number of fields using feeds from the health plan's database and the patient's EMR which may be contained in or accessed by the healthcare providers system or the health plan's database (or some third party database that stores EMRs), thereby reducing data input time and minimizing the potential for the introduction of typographical and other data input errors. Examples of automatic completed field include patient height, weight, diagnosis, lab results, previously used medications, quality of life scores, diagnostic test results, and genetic testing results. Menu drop downs and radio boxes are also used to improve accuracy of information and further reduce the input time.

Using the knowledge-base described above, the processor of the inventive system highlights or otherwise flags inputs that fall outside of a health plan's clinical policies ahead of transmission. In particular, the processor evaluates the medically-coded drug orders relative to the health plan's medical benefit policies, as well as the eligibility status and the patient's medical benefit coverage with their health insurer. This allows a healthcare provider to modify inputs that are in accordance with a plan's clinical policies for medication use, or submit as-is because of unique patient needs.

Data Feeds Interface (42)

The Data Feeds Interface is a data processing interface which is transparent to end users. It is integrated with the database platform in the RX Specialty HUB system. As a stand-alone system, apart from various health plan systems, a patient's health plan eligibility data is provided to RX Specialty HUB on a periodic basis, preferably daily 42'. Drug specific, health plan-specific clinical policies are also provided periodically, preferably weekly or monthly 42". The RX Specialty Hub system may also connect with a healthcare provider's EMR software or other clinical data vendors for data feeds 42'''. Additionally, as indicated above, claims paid by the health plan are also electronically submitted to RX Specialty Hub in the HCFA 1500 data set 42'''. Data is integrated into RX Specialty HUB's SQL database for data processing. The clinical rules supplied by the plan may be updated incrementally depending on frequency and volume of changes. It will be appreciated that the RX Specialty HUB system could also be implemented within a health plan's system rather than as a stand-alone system.

Eligibility Decision (355)

The "Eligibility Approval Interface" is database query check used to process the request and is another transparent interface to the users of the RX Specialty HUB system. This interface uses a logic engine 44', such as branching logic, to determine patient eligibility.

As part of the adaptive intake form, a healthcare provider is prompted to select the patient's health plan and drug requested from drop down menus. The healthcare provider is then prompted to enter the patient name and birth date. Using these initial inputs and the Health Plan Eligibility Data Feed, the Real Time Decision Interface determines if a patient is eligible for a prior authorization request using the system. If the patient is eligible, the adaptive intake form uses the inputs to generate the rules based intake form specific to patient, drug, and health plan clinical policies. If the patient is not eligible to continue, the healthcare/medical service provider is notified and a time/date stamp is applied to the transaction and stored as part of the MD Dashboard.

Pending Medical Management Decision (360)

Once a healthcare provider has completed entering all information need as part of the Real Time Decision Interface, one of two possible decisions will be made and a request will have a "Pending for Medical Management Review Decision" 360 or the request will have a "Prior Authorization Approval Decision". A "Pending Medical Management Review Decision" triggers a notification that is returned immediately to the requesting healthcare provider and displayed on the MD dashboard during the session. This notification specifically states that the request is "Pending Medical Management Review." All patient requests (approved and pending) per healthcare provider are listed on a healthcare provider "MD Dashboard" report. The MD Dashboard report shows a summary of each request and request approval status (Approved or Pending Medical Management Review).

The other pended-request notification is sent to the health plan's medical management staff and stored in the "Health Plan Medical Management Reviewer Dashboard". Medical Management reviewers are notified preferably via as part of a direct Health Plan Interface log in. Notifications to the health plan may also be sent via e-mail or facsimile.

Health Plan Medical Management Reviewer Dashboard (52b)

After the Real Time Decision Interface determines if a prior authorization request is outside of a health plan's clinical policies, a copy of the inputs are docketed into the "Health Plan Medical Management Reviewer Dashboard" 52b. Medical management reviewers from each health plan log into their dedicated dashboard via secure authentication and are able to view all pended requests as well as view their health plan's clinical policies. They are then able to determine if a request should be approved or denied. Using checkboxes, a reviewer can provide a disposition for each request, i.e., "approve" or "deny" the request.

If a request is approved, a referral form is generated and sent electronically or via fax to the specialty pharmacy selected as part of the intake form generation by the healthcare provider. The healthcare provider is notified via email and as part of the MD Dashboard that a request has been approved. The specialty pharmacy then calls the healthcare provider to create a verbal prescription and the medically coded drug is dispensed per instructions.

If a request is denied, a notification is generated via email and via MD Dashboard to the healthcare provider. The process ends at this point.

Health Plan Medical Management Reviewer Interface (84)

The Health Plan Medical Management Reviewer Interface 84 is used by the medical management reviewer to access the health plan's specific restricted area. As described above with reference to the MD Interface, secure access to the system is the preferred method of operation for the RX Specialty HUB system. Upon entry into the Health Plan Medical Management Review Interface, the reviewer has access to view a healthcare provider's adaptive intake form and determining whether to approve or deny pended requests. All requests and decisions are stored in the Health Plan Medical Management Reviewer Dashboard. Once a decision is made, the healthcare provider is notified of the decision via email and in the MD Dashboard. If the request is approved, the adaptive intake form inputs are used to generate a referral form which is sent to the specialty pharmacy previously identified by the healthcare provider. If the request is denied, the healthcare provider is notified via email and in the MD Dashboard.

Prior Authorization Approval Decision (18')

The "Prior Authorization Approval Decision" 18' is a decision made using the knowledge base of the Real Time Decision Interface. Once a request is approved the healthcare provider is notified and a unique authorization code or other transaction-specific ID is assigned to the approved request. The adaptive intake form is used to generate a Specialty Pharmacy Referral Form that is sent to the dispensing pharmacy to dispense the drug as prescribed. Information regarding the pharmacy would be collected at the time the initial adaptive intake form was completed. Facsimile, e-mail, and the Specialty Pharmacy Dashboard are primary mechanisms to notify pharmacies of approvals. E-prescribing capabilities are built also into RX Specialty Hub and use all necessary protocol. Therefore, with a pharmacy-specific portion of the RX Specialty HUB application the prescription delivery can be entirely automated by, processed through and maintained within the RX Specialty HUB system.

Specialty Pharmacy Dashboard (52c)

After the Real Time Decision Interface determines that a prior authorization request is within a health plan's clinical policies, the unique identifier or transaction-specific authorization code is assigned to the request, the Specialty Pharmacy Referral Form is generated, and a copy of the inputs are sent to the "Specialty Pharmacy Dashboard" 52c. Users from each specialty pharmacy log into their Dashboard via Specialty Pharmacy Interface 86 and are able to view all approved requests as well as each health plan's clinical policies. They are then prompted to call the physician, verify the prescription, and dispense the medically coded drug as prescribed and approved. In the event that a physician is purchasing the medically-coded medication, the physician is identified as the specialty pharmacy.

If a request had been previously outside of a health plan's clinical policies and subsequently approved by a health plan medical management reviewer, an electronic prescription or referral form is generated when the health plan reviewer approves the request. The same process as described above is used and a Specialty Pharmacy Referral Form is generated and sent electronically or via fax to the specialty pharmacy selected and their Specialty Pharmacy Dashboard. The healthcare provider is notified via email and as part of the MD Dashboard that a request has been approved. The specialty pharmacy then calls the healthcare provider to create a verbal prescription and the medically coded drug is dispensed per instructions.

Once dispensed, the NDC of the medically coded drug and the vial size, strength, and number of vials dispensed is entered into the Specialty Pharmacy Dashboard by the dispensing Specialty Pharmacy.

Specialty Pharmacy Interface (86)

The Specialty Pharmacy Interface is used by the pharmacy to process a medically-coded drug authorization request that RX Specialty Hub's Real Time Decision Interface has determined to be within a health plan's clinical policies. As described above with reference to the MD Interface, a web-based application is the preferred method of operation for the RX Specialty HUB system, and it will be appreciated that a request can be called into RX Specialty Hub and processed by a RX Specialty Hub specialist or customer service representative. Accordingly, the communication channel or link is secured by the use of the user ID and password requirements for accessing the Real Time Decision Interface as well as other security protocols that can be used for receiving information via telephone. For medically coded drugs, the Specialty Pharmacy Interface allows for real-time connectivity to the healthcare provider's inputs of patient and drug specific criteria, as well as to a health plan's clinical policies. As with the MD Interface, transactions are preferably conducted electronically to reduce turn-around time.

J-Code/NDC Conversion Cross-Walk (44")

The interfaces for the J-Code/NDC Conversion Cross-Walk 44" allow the medically-coded drugs, such as those assigned a J-code, to be converted to NDC. The RX Specialty Hub system uses two files to perform the J-code to NDC crosswalk. One file is a medical claims paid file which is provided by the health plan and includes the patient specific unique authorization number or other code that RX Specialty Hub had assigned when the medication request had been approved for dispensation. The other file is a Drug Dispensation file which is provided by the specialty pharmacy either through a separate report or as one of the inputs collected in the Specialty Pharmacy Dashboard and includes the same patient specific unique authorization code that RX Specialty Hub had provided to the specialty pharmacy to link the dispensed medication with the particular drug order submitted by the healthcare provider.

The Rx Specialty Hub system reconciles specialty pharmacy and health plan data feeds to create a J-code to NDC conversion, i.e., reconcile the medically-coded drugs with the prescription NDC drug codes. Once the NDC is assigned, volumes of medications dispensed per NDC are calculated by the RX Specialty HUB system. These calculations create measureable rebate opportunities that health plans may have in their contracts with pharmaceutical manufacturers.

The cross-walk process is generally not executed in real time. Instead, it is processed after the medically-coded drugs have been ordered and dispensed and a reasonable period of time is given for a claim to be submitted to the health plan for reimbursement. Accordingly, the cross-walk processing may occur approximately 30-60 days after the medically-coded drug has been dispensed. The Rx Specialty Hub system uses a match between the authorization code from the specialty pharmacy and the authorization code from original request from the healthcare provider. The health plan may be required to submit HCFA 1500 data feeds for the in the cross-walk.

Patient Exchange (54)

RX Specialty Hub allows physicians 30 to provide patients 32 with and print education materials, websites, and links to advocacy groups 56 once a patient's prior authorization request has been approved. Patient materials are provided to improve education and understanding of disease, medication prescribed, and medication administration. By providing education materials, patients are more compliant to their medication. Safety for patients is also improved by providing additional information such as a Food and Drug Administration (FDA) approved drug monograph. Drug monographs represent published standards for the use of one or more substances.

In addition to providing medication and disease related materials for patients, compliance tools such as an email reminder 56' and/or calendar invite 56" reflecting drug administration schedules can be programmed for patients, and transmitted directly to the patient. Other compliance tools that can be provided as part of the patient exchange include hard copy schedule of administration, information to advocacy groups, copay assistance foundation information, or additional information dedicated to help patients maintain compliance to their medications.

Reporting Suite

The RX Specialty HUB permits the creation of specialized reports that had not been previously available using manual processes. With the automated and integrated RX Specialty HUB system, its sharing of data and feedback loops, specialty drug reports can be provided to health plans, medical offices, pharmaceutical manufacturers, and specialty pharmacies. Reports can readily be formulated and automatically generated based on the particular requirements of these parties, and can be delivered via secure FTP, secure e-mail or accessed within the system's dashboards. The data created and accumulated through the RX Specialty Hub system would be de-identified at the member level before it is made available to pharmaceutical manufacturers as reports from the system. Several examples of reportable metrics are listed in the table below.

| Type | Report | Chart | Frequency |
|---|---|---|---|
| Overview | Total # of referrals in Quarter | | Q |
| | Referrals by Therapeutic Class | yes | Q |
| | Referrals by Class, by Brand | yes | Q |
| | Members in each Class | yes | Q |
| | Trend: referrals vs. last quarter | yes | Q |
| | Trend: within each therapeutic class | yes | Q |
| Detail | Referrals by Geography | map | Q |
| | Member breakdown by Group | yes | Q |
| | Therapeutic Class: breakdown by Drug | yes | Q |
| | Therapeutic Class: breakdown by Member | | Q |
| | Therapeutic Class: breakdown by Physician | | Q |
| | Therapeutic Class: breakdown by Site of Care | yes | Q |
| | Therapeutic Class: breakdown by Admin Auth | | Q |
| | Therapeutic Class: breakdown by diagnosis | | |
| | Pharmacy Provider Detail | yes | Q |
| Op Metrics | # Authorized | | Q |
| | # Pending Review by Health Plan Reviewer | | Q |
| | Eventual Approvals vs Denials on Pending | yes | Q |
| | Speed to Auth | | Q |
| | Average time in Pend Que | | Q |
| | Speed to answer Customer Service Calls | | Q |
| Financial | J-Code to NDC Crosswalk | | Q/A |
| | Therapeutic Class: Market Share of Brands | yes | Q/A |
| | Therapeutic Class: PMPM cost | | A |
| | Member PMPM Costs by Group | | A |
| Trend Analysis/ Recommendation | Policy Changes, Edits | | Q/A |
| | Site of Care | | Q/A |
| | Manufacturer Contracting | | Q/A |
| | Pharmacy Provider Contracting/Audit | | Q/A |
| Intervention | Quantify value of prospective hub | | Q/A |

Screen Shots of RX Specialty HUB Application

The RX Specialty HUB web link would be used by the healthcare providers to make online prior authorization requests. The healthcare providers would log in securely through an access portal screen as displayed in FIG. 4.

Figures 6A, 6B:
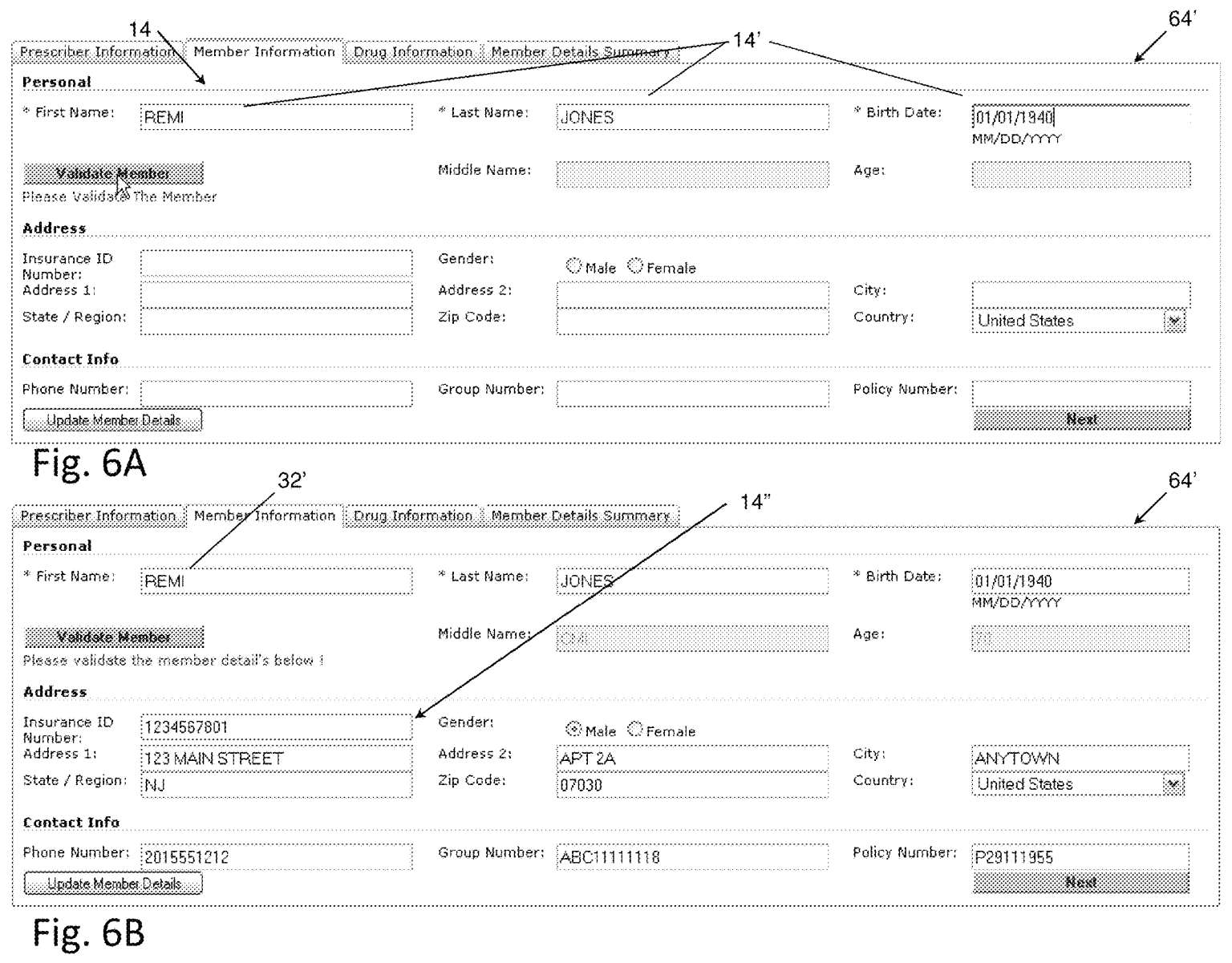

The healthcare provider selects the health plan, medically-coded drug or disease state, and treatment required for the patient using drop down menus as shown in FIG. 5. The healthcare provider information would be listed in the Prescriber Information tab on the primary RX Specialty HUB interface screen as shown in FIG. 6A. The patient would be identified on the Member Information tab on the RX Specialty HUB interface screen, and their information would then be automatically uploaded to the screen as shown in FIG. 6B so that the healthcare provider could confirm that the correct patient is listed. When the healthcare provider selects the Validate Member radio button, the patient information is run through the authentication and validation evaluations as discussed above for the particular medically-coded drug that the healthcare provider had selected in the previous step. The RX Specialty HUB system is able to make this determination typically within five (5) minutes in most instances with most evaluations being performed within one (1) to ten (10) minutes. Information regarding the diagnosis would be collected using drop down fields and database queries.

Figure 8:
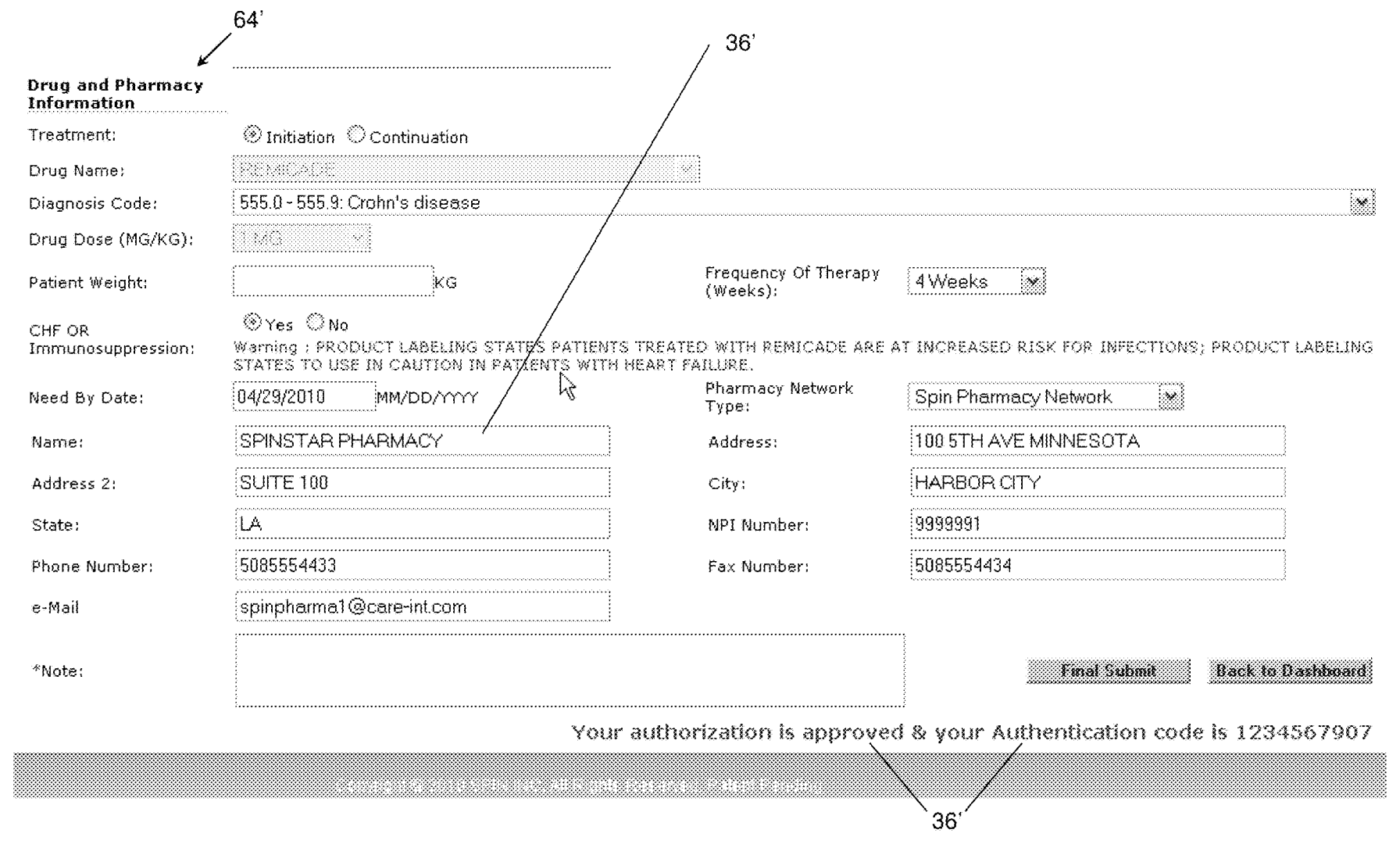

As shown in FIG. 7, drug specific criteria are selected using a drop-down menu of ICD-9 diagnosis codes and the therapy status for the patient can be selected using radio buttons for initiating therapy or continuing therapy. The RX Specialty HUB system already has the information on the patient weight and maintains a knowledge-base with other selectable criteria. Accordingly, the drug dosage, therapy duration, and the pharmacy network are entered using menu driven fields. The RX Specialty HUB system also tracks the need by date for the medically-coded drug. An adaptive intake form using branching logic is preferably used to create specific inputs required to determine therapy approvability. The healthcare provider selects the Validate Prescription button, and the RX Specialty HUB Real Time Decision Interface automatically evaluates all of the inputted criteria against clinical policies and guidelines approved by the health plan to determine whether the drug authorization is approved or whether it requires further review by a health plan's medical management. FIG. 8 shows the Drug and Pharmacy Information screen that appears when the drug authorization is approved. This screen displays the Authentication Code for the transaction which is the unique authorization code that is assigned to the authorization approval from the health plan and the order that is placed with the specialty pharmacy for the medically-coded drugs.

Figure 9A:
Figure 9B:
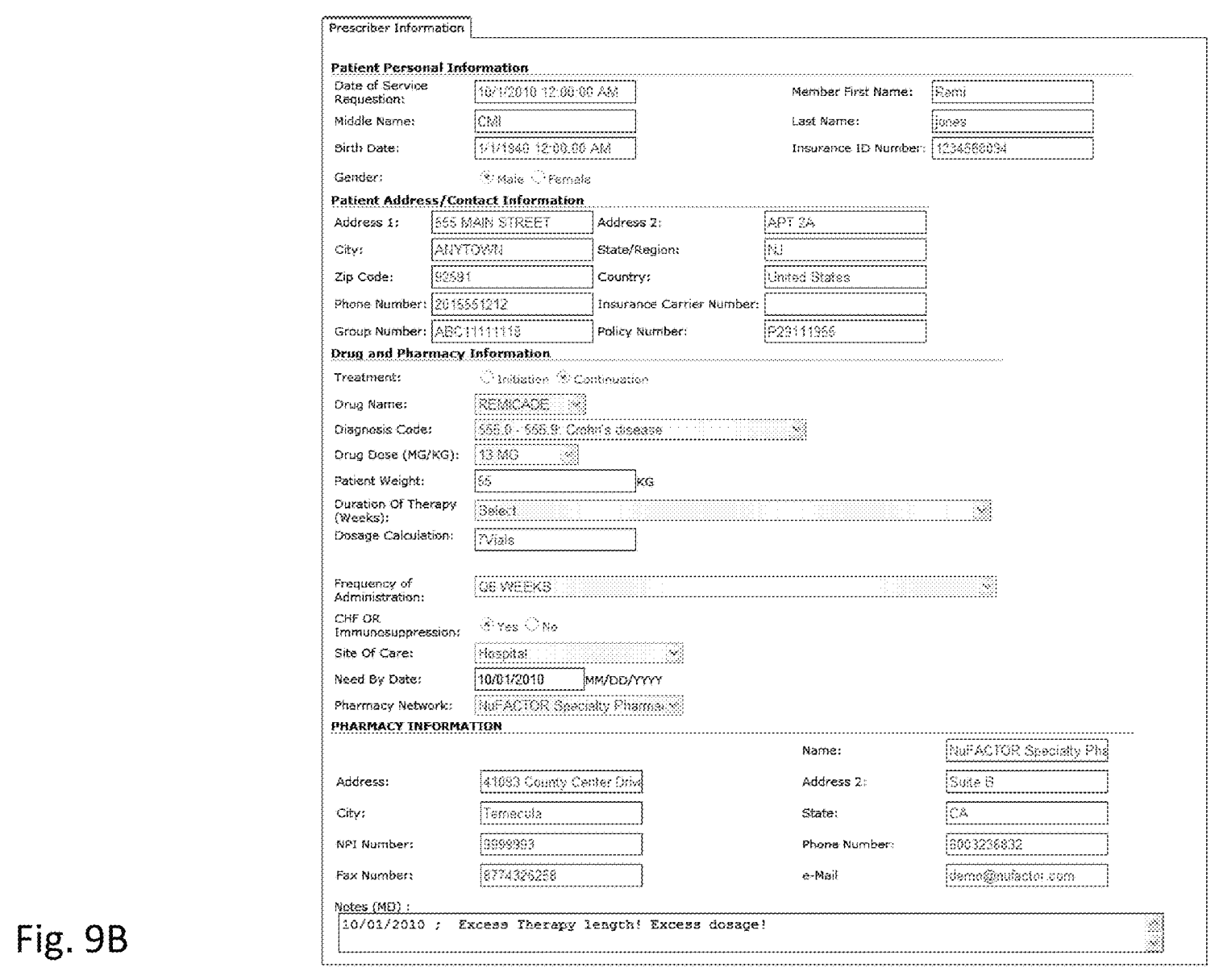
Figure 9C:
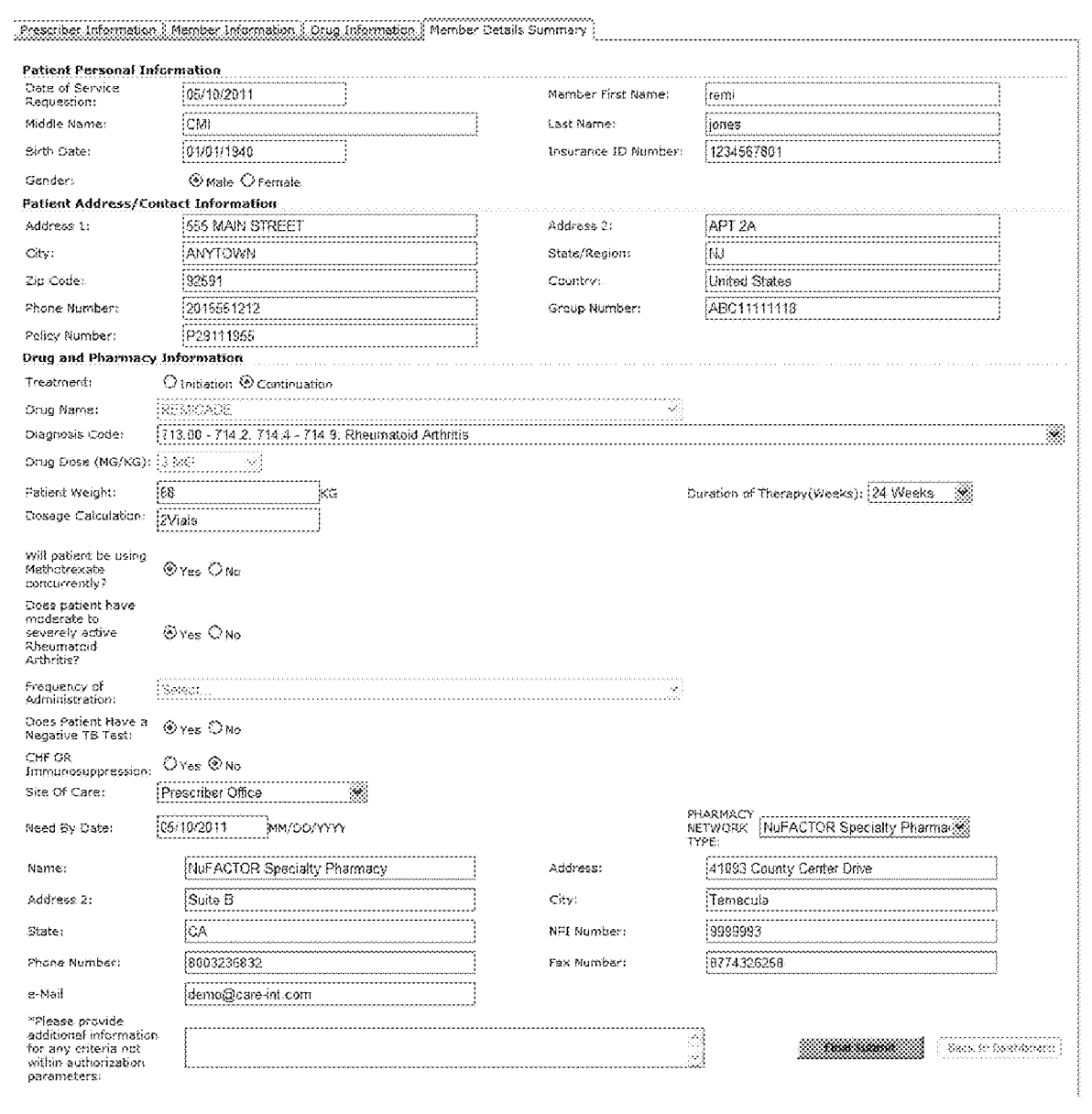

The MD Dashboard uses the information that it collects and tracks to provide reports for the healthcare provider. For example, the report in FIG. 9 shows a summary and current status of the requested authorizations that a healthcare provider ("prescriber") has processed through the RX Specialty HUB system.

Figure 10:
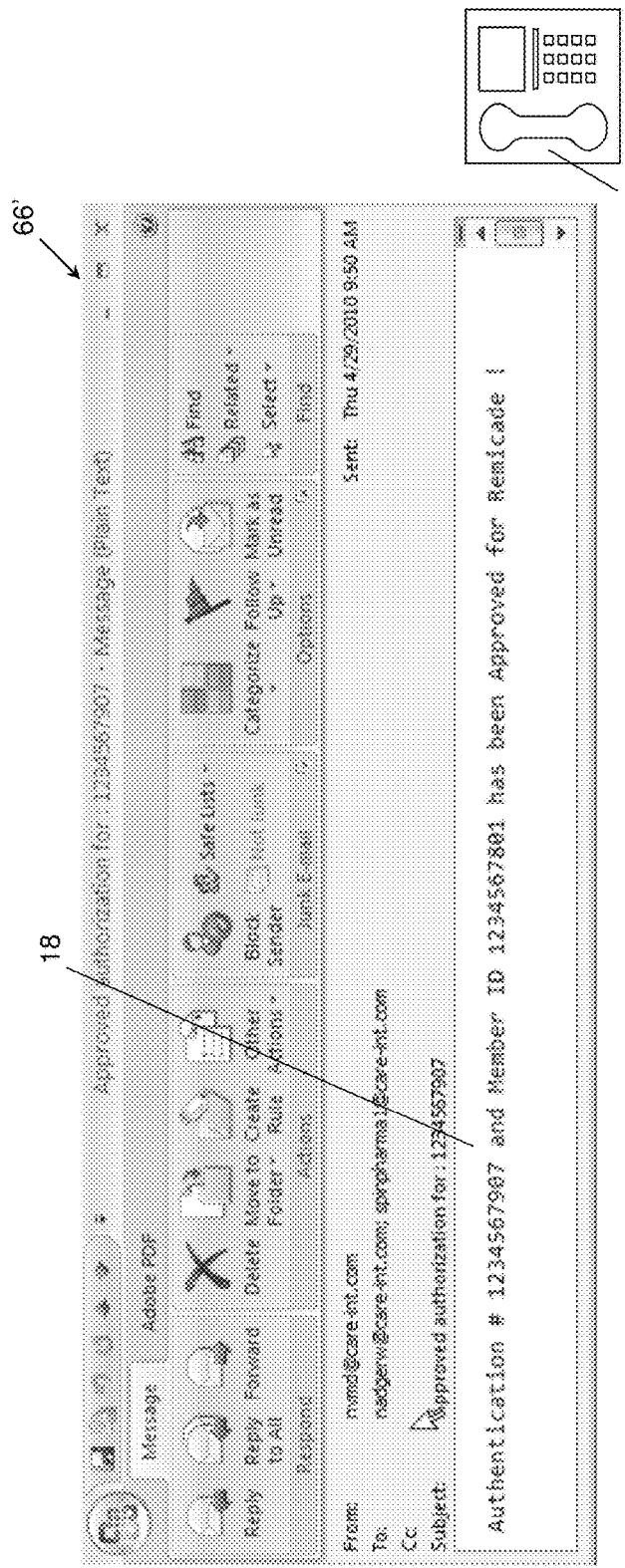

As discussed above and shown in FIG. 10, the RX Specialty HUB system can generate an email confirmation for each approved authorization that is sent to the healthcare provider and the specialty pharmacy.

Figure 11:
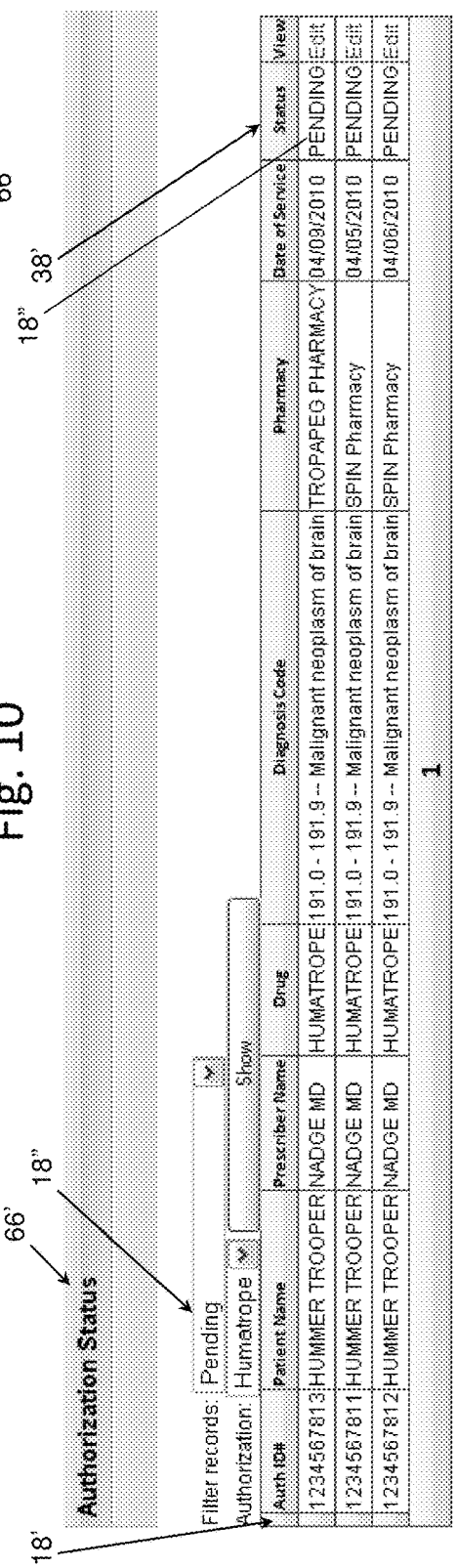

The RX Specialty HUB system also gives the health plan's medical reviewer the ability to view pending authorizations that require further review using the Health Plan Medical Management Reviewer Interface. As shown by FIG. 11, the medical reviewer can filter the authorizations based on various selection criteria and track tasks as part the Health Plan Medical Management Reviewer Dashboard.

The health plan's medical reviewer can view pending authorizations that require further assessment, and can approve or deny dispensation of the drug. If the reviewer approves dispensation of the medically-coded drug, a notification is provided to the healthcare provider as part of their MD Dashboard, and a referral form is generated and sent to the healthcare provider's previously chosen specialty pharmacy and to the Specialty Pharmacy Dashboard. Upon receipt of the referral form, the specialty pharmacies call the healthcare provider to verify the dosage and administration of the medication. This process creates a verbal prescription used by the specialty pharmacy to fill the medication. At this point, the process is closed until a "continuation" of therapy request is created within the system.

From the preceding description of the RX Specialty HUB system, it is evident that the present invention has a number of features and functionality which are not found in current systems and processes, including the unique aspects of the invention listed in the table below.

Unique Features & Functions of Invention
  Real Time prior authorization processing specific to health plan policies, prescriber needs, and patient needs
  Tiered formulary management of Specialty/Biological Drugs and rebate generation opportunities Rebate capture by creating a J code to NDC crosswalk and conversion (linking quantity of dispensed drug to NDC number and quantity)

Real time intervention to direct patients to a specific and appropriate site of care (home infusion, hospital infusion, physician office infusion)

Drug specific deterministic criteria based ICD-9 diagnosis, initiation or continuation of therapy, and on industry/evidence based guidelines Clinical Parameters (lab values and other clinical metrics), Site of Care for Medication Administration, and Medication Dispensing information prospectively captured at one time Care Alerts reminding prescribers of precautions needed with usage or administration of medication Drug and disease information, as well as Compliance Reminders transmitted directly to the patient Monitoring capacity to improve appropriate duration of therapy and discontinuation of ineffective medication (includes lab value monitoring, Quality of Life monitoring, and other efficacy metrics)

E-Prescribing

Connectivity and automated transactions to find relevant clinical metrics in a patient's EMR NDC assigned to all medications dispensed as part of a medical benefit Drug specific and market share dispensing analytics Complete patient information provided for Medical Management Review only when parameters are outside of clinical policies Email notification of reminders to physicians and Medical Management Reviewers Consistent referral forms generated for approved request and provided in real time to Specialty Pharmacies for drug fulfillment. Provided via fax, email, or web-based transactions.

Reduced non-approved experimental use of medications

Although some current systems provide utilization management programs with web-based physician authorization programs, they fail to integrate the front end medical office authorization with orders for medically-coded drugs. Accordingly, there is no present system which can automate the process for obtaining approval authorization on medically-coded drugs and track the information on the dispensed medically-coded drugs for rebate collection, nor can any current system provide the healthcare provider with the selection criteria for clinical, site of care, and dispensing inputs using a knowledge-base system. Finally, it will be appreciated that the current systems are still primarily based on the old manual processes rather than the interactive, real-time system of the present invention. Therefore, the current systems typically require days to complete the authorization approval process whereas the RX Specialty HUB system completes the end-to-end authorization approval process within minutes.

It will be appreciated that the particular way in which the knowledge-base is integrated with the interactive ordering system with the feedback system solves the inadequacies of current systems and results not only in benefits that have not been realized before but are unexpected when considering each of the known systems in an individual manner or when merely combining the features of these known systems without integrating the front end authorization approval with the ordering and tracking of the medically-coded drugs that are actually dispensed for the treatment of patients.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A medically-coded drug management computer system for authorizing and confirming administration of a medically-coded drug comprising:
   A. one or more electronic databases, stored on one or more non-transitory computer-readable media, comprising:
      (1) criteria for a plurality of medically-coded drugs associated with a plurality of health plans
      (2) patient identifying information of a plurality of patients associated with said health plans,
      (3) information on a plurality of specialty pharmacies with capabilities to dispense a set of said medically-coded drugs;
      (4) health plan eligibility data for the plurality of patients received from a plurality of health plan data computer nodes located remote from the one or more electronic databases, the health plan eligibility data comprising:
         (i) first set of health plan eligibility data associated with a first health plan and a first health plan data computer node, and
         (ii) second set of health plan eligibility data associated with a second health plan and with a second health plan computer node;
   B. a healthcare provider interface provided by a computing device, the healthcare provider interface including:
      (1) a login interface, provided by the computing device, and
      (2) a data input and review, provided by the computing device,
      wherein the healthcare provider interface, using the computing device, identifies a user as an authorized representative of a corresponding healthcare provider through said login interface,
      wherein said data input and review interface is configured to receive input data and provide said input data to said one or more electronic databases and to receive data stored in said one or more electronic databases for presentation to the authorized representative on the computing device,
      wherein said input data comprises:
         (i) an authorization request including data that identifies a patient from said plurality of patients,
         (ii) a selection of a drug from said plurality of drugs, and
         (iii) a choice of a specialty pharmacy from said plurality of said specialty pharmacies;
   C. a prospective drug access generator, provided on a computing device, comprising an automated data processor, and in operative communication with said one or more electronic databases and said computing device including the healthcare provider interface, wherein said prospective drug access generator comprises
(i) logic engines configured to:
determine whether the drug selected is authorized for said identified patient, where the logic engines determine whether the drug selected is authorized based on:
the authorization request received from the healthcare provider interface including the data that identifies the patient; and
respective health plan eligibility data associated with the patient identified in the authorization request, and
providing a unique authorization code with a relational link between said identified patient, said selected drug and said healthcare provider on the condition that the identified patient is authorized to receive the selected drug;
wherein the determination is made prospectively before the unique authorization code is produced and before the drug selected is dispensed,
the prospective drug access generator receiving, via the computing device, a pharmacy dispensing report from a computer node associated with the chosen specialty pharmacy, the pharmacy dispensing report associated with the authorization code and providing a pharmacy confirmation that the selected drug was dispensed to the healthcare provider,
the prospective drug access generator receiving, via the computing device, a medical claims report from said computing device including said healthcare provider interface,
said medical claims report said authorization code and including information including a medical confirmation that said selected drug was administered to said identified patient,
said prospective drug access generator calculating, using the second computing device, utilization data corresponding to the pharmacy dispensing report and the medical claims report, and storing the utilization data in the one or more electronic databases.

2. The system of claim 1, wherein said prospective drug access generator transmits the authorization code through an authorization interface of the healthcare provider interface via the computing device,
wherein said login interface is at least one of a web-enabled login screen and a telephonic keypad-entry login prompt,
wherein said data input and review interface is at least one of a web-enabled data screen, a telephonic keypad-entry data prompt and a telephonic headset data report, and
wherein said authorization interface is at least one of a web-enabled authorization screen and a telephonic headset authorization report.

3. The system of claim 2, wherein the pharmacy dispensing report is transmitted over a secure communication channel comprising at least one of a web-enabled communication link and a telephonic communication link.

4. The system of claim 3, wherein said prospective drug access generator generates an adaptive intake form based on patient specific metrics and drug-specific criteria provided from the one or more electronic databases to complete fields of the adaptive intake form.

5. The system of claim 4, wherein said prospective drug access generator uses said patient specific metrics and drug specific criterial to retrieve information, using the computing device, from said one or more electronic databases and automatically completes a plurality of fields in said adaptive intake form by inserting retrieved data.

6. The system of claim 5, wherein only inputs that are required are prompted for said user to enter, and
wherein said adaptive intake form is used to generate a referral form corresponding to said healthcare provider and said chosen specialty pharmacy.

7. The system of claim 1, further comprising:
a healthcare provider dashboard, a health plan dashboard and a specialty pharmacy dashboard provided on the computing device,
wherein each of said dashboards comprises a respective docket and each of said dockets summarizes information from said one or more electronic databases,
wherein said docket for said healthcare provider dashboard is further comprised of an authorization request docket having a status report with a tracking of approved and pending authorization requests and an identification of pending tasks for completion,
wherein said health plan dashboard is further comprised of a store of prior authorization requests, a viewer of a plurality of completed intake forms and clinical policies corresponding with said health plans, a task tracker and a medical management review interface, and
wherein said specialty pharmacy dashboard comprises a report of approved requests tasked to the pharmacy for dispensation with a status of said request according to a need-by date.

8. A medically-coded drug management computer system for authorizing and confirming administration of a medically-coded drug comprising:
A. one or more electronic databases, stored on one or more non-transitory computer-readable media, comprising:
(1) criteria for a plurality of drugs associated with a plurality of health plans
(2) patient identifying information of a plurality of patients associated with said health plans,
(3) information on a plurality of specialty pharmacies with capabilities to dispense a set of said medically-coded drugs;
(4) health plan eligibility data for the plurality of patients received from a plurality of health plan data computer nodes located remote from the one or more electronic databases, the health plan eligibility data comprising
(i) a first set of health plan eligibility data associated with a first health plan and with a first health plan data computer node, and
(ii) a second set of health plan eligibility data associated with a second health plan and with a second health plan computer node;
B. a healthcare provider interface provided on a computing device, the healthcare provider interface including:
(i) a data input and review screen, provided by the computing device, configured to enable an authorized healthcare provider to submit input data to said one or more electronic databases and to access stored data in said one or more electronic databases,
wherein said input data comprises
(i) an authorization request that identifies a patient from said plurality of patients, selects a drug from said plurality of drugs, and chooses a specialty pharmacy from said plurality of said specialty pharmacies;
C. a prospective drug access generator, provided on the computing device, comprising an automated data processor and in operative communication with said one or more electronic databases and said computing device including said healthcare provider interface, wherein said prospective drug access generator comprises:
  logic engines configured to determine whether the drug is authorized for said identified patient, where the logic engines determine whether the drug is authorized based on:
  the authorization request received from the healthcare provider interface including data that identifies the patient;
  respective health plan eligibility data associated with the patient identified in the authorization request, and
  said prospective drug access generator provides, using the computing device, a unique authorization code with a relational link between said identified patient, said selected drug and said healthcare provider on the condition that the identified patient is authorized to receive the selected drug,
  wherein the determination is made prospectively before the unique authorization code is produced and before the drug selected is dispensed,
  said prospective drug access generator calculating, using the computing device, utilization data corresponding to a pharmacy dispensing report and a medical claims report and updates said one or more electronic databases with said utilization data;
  the prospective drug access generator receiving, by the computing device said pharmacy dispensing report from a computer node associated with said chosen specialty pharmacy,
  said pharmacy dispensing report associated with said authorization code and providing a pharmacy confirmation that said selected drug was dispensed to said authorized healthcare provider; and
  the prospective drug access generator receiving, via the computing device, a medical claims report from said authorized healthcare provider computer node,
  said medical claims report including said authorization code and provides information including a medical confirmation that said selected drug was administered to said identified patient,
  said prospective drug access generator calculating, using the computing device, utilization data corresponding to the pharmacy dispensing report and the medical claims report, and updating, via the computing device said one or more electronic database with the utilization data.

9. The system of claim 8, wherein said logic engines utilize a branching logic process.

10. The system of claim 8, wherein said healthcare provider interface produces an adaptive intake form based on patient-specific metrics and drug-specific criteria to complete fields of the adaptive intake form.

11. The system of claim 10, wherein said prospective drug access generator retrieves information from said one or more electronic database, based on said patient specific metrics and drug specific criteria, using the computing device and automatically completes fields of the adaptive intake form using the retrieved information.

12. The system of claim 11, wherein only inputs that are required are prompted for said authorized healthcare provider to enter in the adaptive intake form, and
  wherein said authorized healthcare provider selects from a private session for logging into said healthcare provider interface and a proxy session in which said authorized healthcare provider telephonically communicates with a centralized proxy user and said proxy user logs into said healthcare provider interface on behalf of said authorized user,
  wherein said proxy user has a set of credentials known to said healthcare provider interface to act on behalf of a plurality of authorized users.

13. The system of claim 10, wherein said adaptive intake form is used to generate a referral form corresponding to said authorized healthcare provider and said chosen specialty pharmacy.

14. The system of claim 8, further comprising:
  a patient exchange in operative communication with said database, a healthcare provider dashboard, a health plan dashboard and a specialty pharmacy dashboard,
  wherein each of said dashboards comprises a respective docket and each of said dockets summarizes information from said database.

15. The system of claim 14, wherein said patient exchange further comprises a set of electronic communication tools selected from the group consisting of: print education materials, websites, and links to advocacy groups, drug monographs, messaging on defined therapies, e-mail correspondence, reminders, calendar invitations, and any combination thereof.

16. The system of claim 14, wherein said docket for said healthcare provider dashboard is further comprised of an authorization request docket having a status report with a tracking of approved and pending authorization requests and an identification of pending tasks for completion,
  wherein said health plan dashboard is further comprised of a store of prior authorization requests, a viewer of a plurality of completed intake forms and clinical policies corresponding with said health plans, a task tracker and a medical management review interface, and
  wherein said specialty pharmacy dashboard comprises a report of approved requests tasked to the pharmacy for dispensation with a status of said request according to a need-by date.

17. The system of claim 8, further comprising a reconcilator configured to generate an accumulation of said utilization data based on a plurality of utilization data from a plurality of pharmacy dispensing reports and a plurality of medical claims reports associated with a plurality of respective authorization codes, and
  a reconcile rebate amounts according to said accumulated utilization data.

18. A medically-coded drug management computer system for authorizing and confirming administration of a desired dose of a medically-coded drug comprising:
  A. one or more electronic databases, stored on one or more non-transitory computer-readable media, comprising:
    (1) criteria for a plurality of drugs associated with a plurality of health plans,
    (2) patient identifying information of a plurality of patients associated with said health plans,
    (3) information on a plurality of specialty pharmacies with capabilities to dispense a set of said drugs;
    (4) health plan eligibility data for the plurality of patients received from a plurality of health plan data computer nodes located remote from the one or more electronic databases, the health plan eligibility data comprising
      (i) a first set of health plan eligibility data associated with a first health plan and with a first health plan data computer node, and
      (ii) a second set of health plan eligibility data associated with a second health plan and with a second health plan computer node;
  B. a healthcare provider interface, provided on a computing device, comprising:

(1) a telephonic keypad entry login prompt, provided by the computing device,
(2) a telephonic data input prompt and telephonic headset data report, provided by the computing device, and
(3) a telephonic headset authorization report, wherein a user is identified as an authorized representative of a corresponding healthcare provider through said login prompt on the computing device, wherein said authorized healthcare provider inputs data to and accesses stored data in said one or more electronic databases through said data input prompt and headset report, using the computing device, wherein said input data comprises an authorization request that that includes data that identifies a patient from said plurality of patients, selects a drug from said plurality of drugs, and chooses a specialty pharmacy from said plurality of said specialty pharmacies;

C. a prospective drug access generator, provided on the computing device, comprising an automated processor and in operative communication with said database and said healthcare provider interface, said prospective drug access generator comprises logic engines configured to determine whether the drug is authorized for said identified patient based on health plan eligibility data, and when authorized, said logic engines of said prospective drug access generator determine whether the drug is authorized based on:

the authorization request received from the healthcare provider interface that includes the data that identifies the patient;

respective health plan eligibility data associated with the patient identified in the authorization request, and the prospective drug access generator providing a unique authorization code with a relational link between said identified patient, said selected drug and said healthcare provider on the condition that the identified patient is authorized to receive the selected drug;

wherein the determination is made prospectively before unique authorization code is produced and before the drug selected is dispensed, the prospective drug access generator receiving a pharmacy dispensing report from said chosen specialty pharmacy, wherein said pharmacy dispensing report is associated with said authorization code and provides information including a pharmacy confirmation that said selected drug was dispensed to said healthcare provider; and the prospective drug access generator receiving a medical claims report from said authorized representative of said healthcare provider, wherein said medical claims report including said authorization code and provides information including a medical confirmation that said selected drug was administered to said identified patient, and wherein said prospective drug access generator calculates utilization data corresponding to the pharmacy dispensing report and medical claims report, and transmits the utilization data to the one or more electronic databases for storage.

\* \* \* \* \*